(12) United States Patent
Snyder et al.

(10) Patent No.: US 11,890,389 B2
(45) Date of Patent: Feb. 6, 2024

(54) MOBILE APPARATUS AND METHOD FOR STERILIZING ONE OR MORE SURGICAL TRAYS WITH INTEGRABLE TRANSFER AND STORAGE SYSTEM

(71) Applicant: Progressive Sterilization, LLC, St. Petersburg, FL (US)

(72) Inventors: Barry M. Snyder, Hahira, GA (US); Clarence J. Snyder, III, Theresa, NY (US); Michele Mauzerall, St. Petersburg, FL (US); Maryellen Keenan, Nutley, NJ (US)

(73) Assignee: Progressive Sterilization, LLC, St. Petersburg, FL (US)

( * ) Notice: Subject to any disclaimer, the term of this patent is extended or adjusted under 35 U.S.C. 154(b) by 429 days.

(21) Appl. No.: 17/089,606

(22) Filed: Nov. 4, 2020

(65) Prior Publication Data

US 2021/0046202 A1 Feb. 18, 2021

Related U.S. Application Data

(63) Continuation of application No. 16/212,579, filed on Dec. 6, 2018, now Pat. No. 10,828,383, which is a
(Continued)

(51) Int. Cl.
*A61L 2/20* (2006.01)
*A61L 2/07* (2006.01)
(Continued)

(52) U.S. Cl.
CPC .............. *A61L 2/20* (2013.01); *A61B 50/13* (2016.02); *A61L 2/07* (2013.01);
(Continued)

(58) Field of Classification Search
CPC . A61L 2/20; A61L 2/07; A61L 2/0023; A61L 2202/122; A61L 2202/16; A61L 2202/24; A61B 50/13; A61B 2050/105
See application file for complete search history.

(56) References Cited

U.S. PATENT DOCUMENTS

| 3,088,180 A | 5/1963 | Lauterbach |
| 4,247,517 A | 1/1981 | Sanderson et al. |
| (Continued) | | |

FOREIGN PATENT DOCUMENTS

| CN | 201050842 | 4/2008 |
| DE | 3202430 | 7/1983 |
| (Continued) | | |

OTHER PUBLICATIONS

Anonym: 11 Druckgesteuert—waschbar—zerlegbar 11, Wagner-Steriset, Retrieved from the Internet: URL:http://www.wagner-steriset.de/fileadmin/pdf/SterisetPCD034.pdf, Apr. 5, 2013 [retrieved on Oct. 5, 2017].
(Continued)

*Primary Examiner* — Sean E Conley
(74) *Attorney, Agent, or Firm* — Levine Bagade Han LLP

(57) ABSTRACT

An improved mobile apparatus for sterilizing surgical trays serves as a self-contained autoclave, allowing sterilization of the interior of the apparatus and its contents. A method of sterilization using the apparatus is presented as well. By means of a dedicated transfer and storage system, the apparatus, integrable with respect to a transfer cart and a lift device, may be moved easily between a location of sterilization, a storage area, and an operating room, and more than one such apparatus may be stacked vertically for storage to enhance storage efficiency.

18 Claims, 20 Drawing Sheets

Related U.S. Application Data continuation of application No. 15/608,739, filed on May 30, 2017, now Pat. No. 10,179,183, which is a continuation of application No. 15/411,361, filed on Jan. 20, 2017, now Pat. No. 9,694,093, which is a continuation of application No. 13/944,875, filed on Jul. 17, 2013, now Pat. No. 9,616,143.

(51) Int. Cl.
| | | |
|---|---|---|
| *A61B 50/13* | (2016.01) | |
| *A61B 50/10* | (2016.01) | |
| *A61L 2/00* | (2006.01) | |

(52) U.S. Cl.
CPC ....... *A61B 2050/105* (2016.02); *A61L 2/0023* (2013.01); *A61L 2202/122* (2013.01); *A61L 2202/16* (2013.01); *A61L 2202/24* (2013.01)

(56) References Cited

U.S. PATENT DOCUMENTS

| | | |
|---|---|---|
| 4,251,482 A | 2/1981 | Sanderson et al. |
| 4,450,968 A | 5/1984 | Muellner |
| 4,551,311 A | 11/1985 | Lorenz |
| 4,617,178 A | 10/1986 | Nichols |
| 4,626,971 A | 12/1986 | Schultz |
| 4,643,303 A | 2/1987 | Arp et al. |
| 4,670,227 A | 6/1987 | Smith |
| 4,671,943 A | 6/1987 | Wahlquist |
| 4,704,254 A | 11/1987 | Nichols |
| 4,716,025 A | 12/1987 | Nichols |
| 4,762,688 A | 8/1988 | Berry |
| 4,783,321 A | 11/1988 | Spence |
| 4,915,913 A | 4/1990 | Williams et al. |
| 4,915,918 A | 4/1990 | Nichols |
| 4,955,318 A | 9/1990 | Melhorn et al. |
| 4,997,240 A | 3/1991 | Schmalzl et al. |
| 5,019,345 A | 5/1991 | Lorenz |
| 5,072,960 A | 12/1991 | Sperko |
| 5,202,098 A | 4/1993 | Nichols |
| 5,205,627 A | 4/1993 | Davison et al. |
| 5,223,229 A | 6/1993 | Brucker |
| 5,232,277 A | 8/1993 | Cassady et al. |
| 5,281,400 A | 1/1994 | Berry |
| 5,324,489 A | 6/1994 | Nichols et al. |
| 5,346,075 A | 9/1994 | Nichols et al. |
| 5,352,416 A | 10/1994 | Wagner |
| 5,369,892 A | 12/1994 | Dhaemers |
| 5,372,787 A | 12/1994 | Ritter |
| 5,387,063 A | 2/1995 | Napierkowski et al. |
| 5,415,846 A | 5/1995 | Berry |
| 5,523,519 A | 6/1996 | Weber et al. |
| 5,535,141 A | 7/1996 | Lussi |
| 5,588,623 A | 12/1996 | Leduc |
| 5,732,821 A | 3/1998 | Stone et al. |
| 5,843,388 A | 12/1998 | Arroyo et al. |
| 5,893,618 A | 4/1999 | Lepage et al. |
| 5,923,432 A | 7/1999 | Kral |
| 5,968,459 A | 10/1999 | Nalepa et al. |
| 6,000,486 A | 12/1999 | Romick et al. |
| 6,073,547 A | 6/2000 | Westbrooks et al. |
| 6,164,738 A | 12/2000 | Dane et al. |
| 6,218,796 B1 | 4/2001 | Kozlowski |
| 6,319,479 B1 | 11/2001 | Houston |
| 6,620,390 B1 | 9/2003 | Wagner |
| 6,622,862 B1 | 9/2003 | Corrado |
| 6,789,815 B2 | 9/2004 | Moss et al. |
| 6,867,393 B1 | 3/2005 | Lewis |
| 6,926,874 B2 | 8/2005 | Ongaro |
| 7,001,441 B2 | 2/2006 | Bauer |
| 7,198,760 B1 | 4/2007 | Wagner |
| 7,214,354 B2 | 5/2007 | Ongaro |
| 7,544,915 B2 | 6/2009 | Hu |
| 8,100,281 B2 | 1/2012 | Sands et al. |
| 8,454,901 B1 | 6/2013 | Snyder |
| 8,505,959 B2 | 8/2013 | Darling |
| 9,439,992 B2 | 9/2016 | Webb et al. |
| 9,616,143 B2 | 4/2017 | Snyder et al. |
| 9,694,093 B2 | 7/2017 | Snyder et al. |
| 9,724,439 B2 | 8/2017 | Webb et al. |
| 9,808,545 B2 | 11/2017 | Mauzerall et al. |
| 9,833,524 B2 | 12/2017 | Mauzerall et al. |
| 10,086,100 B1 | 10/2018 | Mauzerall et al. |
| 10,111,972 B2 | 10/2018 | Mauzerall et al. |
| 10,166,305 B2 | 1/2019 | Mauzerall et al. |
| 10,179,183 B2 | 1/2019 | Snyder et al. |
| 10,413,628 B2 | 9/2019 | Mauzerall et al. |
| 10,786,589 B2 | 9/2020 | Mauzerall et al. |
| 10,828,383 B2 | 11/2020 | Snyder et al. |
| 2003/0116636 A1 | 6/2003 | Burkett et al. |
| 2004/0011689 A1 | 1/2004 | Bauer |
| 2004/0096355 A1 | 5/2004 | Ishibiki |
| 2004/0101456 A1 | 5/2004 | Kuroshima et al. |
| 2004/0227315 A1 | 11/2004 | Van Landingham |
| 2005/0132924 A1 | 6/2005 | Bothun et al. |
| 2005/0153052 A1 | 7/2005 | Williams et al. |
| 2006/0032770 A1 | 2/2006 | Orbay et al. |
| 2006/0108757 A1 | 5/2006 | Brookmire et al. |
| 2006/0249313 A1 | 11/2006 | Kamen et al. |
| 2007/0039294 A1 | 2/2007 | Airey |
| 2007/0160494 A1 | 7/2007 | Sands |
| 2008/0063580 A1 | 3/2008 | Von Lersner |
| 2008/0087231 A1 | 4/2008 | Gabriel et al. |
| 2008/0172295 A1 | 7/2008 | Watson |
| 2010/0078905 A1 | 4/2010 | Holtan |
| 2012/0082589 A1 | 4/2012 | Ladison |
| 2013/0272925 A1 | 10/2013 | Ozdamar |
| 2013/0322004 A1 | 12/2013 | Park |
| 2014/0030144 A1 | 1/2014 | Krosney et al. |
| 2014/0079589 A1 | 3/2014 | Landgrebe et al. |
| 2015/0023839 A1 | 1/2015 | Snyder et al. |
| 2015/0078960 A1 | 3/2015 | Krosney et al. |
| 2015/0107627 A1 | 4/2015 | Snyder et al. |
| 2015/0209455 A1 | 7/2015 | Turbett et al. |
| 2015/0209456 A1 | 7/2015 | Turbett |
| 2015/0209462 A1 | 7/2015 | Turbett et al. |
| 2015/0284018 A1 | 10/2015 | Krosney |
| 2015/0314026 A1 | 11/2015 | Mauzerall et al. |
| 2016/0008503 A1 | 1/2016 | Webb et al. |
| 2016/0346415 A1 | 12/2016 | Webb et al. |
| 2017/0080115 A1 | 3/2017 | Mauzerall et al. |
| 2017/0128602 A1 | 5/2017 | Snyder et al. |
| 2017/0189843 A1 | 7/2017 | Turbett et al. |
| 2017/0274107 A1 | 9/2017 | Snyder et al. |
| 2018/0015190 A1 | 1/2018 | Turbett |
| 2018/0021464 A1 | 1/2018 | Mauzerall et al. |
| 2018/0085480 A1 | 3/2018 | Mauzerall et al. |
| 2018/0221803 A1 | 8/2018 | Turbett et al. |
| 2019/0030198 A1 | 1/2019 | Mauzerall et al. |
| 2019/0060494 A1 | 2/2019 | Mauzerall et al. |
| 2019/0175774 A1 | 6/2019 | Snyder et al. |
| 2020/0016289 A1 | 1/2020 | Mauzerall et al. |
| 2020/0030470 A1 | 1/2020 | Mauzerall et al. |
| 2021/0000993 A1 | 1/2021 | Mauzerall et al. |
| 2021/0077640 A1 | 3/2021 | Mauzerall et al. |

FOREIGN PATENT DOCUMENTS

| | | |
|---|---|---|
| DE | 4125673 | 7/1992 |
| EP | 1566185 | 8/2005 |
| EP | 1839683 | 10/2007 |
| FR | 2807325 | 10/2001 |
| JP | 58-068569 U | 12/1981 |
| JP | S56-163341 U | 12/1981 |
| JP | S63-503363 A | 12/1988 |
| JP | H2-136765 U | 11/1990 |
| JP | H4-001380 A | 1/1992 |
| JP | H06-146363 A | 5/1994 |
| JP | H07-505798 | 6/1995 |
| JP | H8-179093 A | 7/1996 |
| JP | 2000-043730 | 8/2001 |
| JP | 2002-019918 | 9/2003 |
| JP | 1184448 | 9/2003 |
| JP | 2002-325826 | 6/2004 |

(56) References Cited

FOREIGN PATENT DOCUMENTS

| JP | 2004-165197 | 6/2004 |
|---|---|---|
| JP | 3127597 U | 12/2006 |
| JP | 2001-112857 | 8/2011 |
| JP | 2012-166747 | 2/2013 |
| WO | WO 1999/049903 | 10/1999 |
| WO | WO 2007/000639 | 1/2007 |
| WO | WO 2010/128408 | 11/2010 |
| WO | WO 2015/153084 | 10/2015 |
| WO | WO 2017/024260 | 2/2017 |
| WO | WO 2019/023710 | 1/2019 |
| WO | WO 2020/005844 | 1/2020 |

OTHER PUBLICATIONS

Anonym: 11 The 134 ~C drain (standard) 11, Wagner Gmbh, Retrieved from the Internet: URL:http://www.wagner-steriset.de/en/the-steriset-system/sterisets-concept/the-134-c-drain-standard/, Apr. 11, 2004 [retrieved on Oct. 6, 2017].
Prophy-Mate. Datasheet (online). NSK, 2002, Retrieved from the internet: URL:http://www.nsktech.com .au/uploads/704 72/ufiles/Prophy_Mate .pdf [retrieved on Aug. 28, 2019].
Wagner Sterilsystem, The SteriSet System, pp. 6-7, May 6, 2005, https://web.archive.org/ web/20050506101217/http://www.wagner-steriset.de/html/mOI E23.htm.
Wagner Sterilsysteme, "Or Filter After All?", pp. 4-5, Aug. 25, 2005, https://web.archive.org/web/20110112052317/http://www.wagner-steriset.de/images/PDFs/Container/Steri Set_Ru ndfi Iter 2003. pdf.
Wagner Sterilsysteme, The SteriSet System, pp. 1-3, Aug. 25, 2005, https://web.archive.org/web/20050825213235/http://www.wagner-steriset.de/html/mOI E21.htm.
The Steris Amsco Sterilization Container System User's Guide, @2003-2006.
Steris Loading Equipment for Amsco Evolution and Evolution—L Steam Sterilizers—North America data sheet, @2011.
AMSCO Material Handling Accessories—Small Sterlizers and Aerators, 2 pages, Sep. 1, 2010, STERIS Corporation.
Getinge 4003 Floor Loading Carts Product Specification, 2 pages, Getinge Group, date unknown.
Operator Manual, AMSCO C Series Small Steam Sterilizers, 154 pages, May 7, 2012, STERIS Corporation.
Operator Manual, AMSCO Century Medium Steam Sterlizer, 186 pages, Jul. 16, 2007, STERIS Corporation.
Operator Manual, AMSCO Century Medium Steam Sterlizers, 135 pages, Dec. 16, 2005, STERIS Corporation.
Scores 510k Summary Pursuant to 21 CFR 807.92, 6 pages, Jul. 26, 2012, AmMed Surgical Equipment, LLC/FDA.
Scores Cabinet Landing Page, 1 page, AmMed Surgical Equipment, LLC, date unknown.
Scores FAQ, 2 pages, AmMed Surgical Equipment, LLC, date unknown.
Scores Instructions for Use, 22 pages, AmMed Surgical Equipment, LLC, , date unknown.
Scores Savings Analysis, 2 pages, AmMed Surgical Equipment, LLC, date unknown.
Scores Testing Summary, 1 page, AmMed Surgical Equipment, LLC, date unknown.
Scores Unit Images in Open Configurations and Landing Page Information About the Scores Unit, 2 pages, AmMed Surgical Equipment, LLC, date unknown.
The Amsco Loading Car and Transfer Carriage—III data sheet, 2 pages, Jul. 10, 1998, STERIS Corporation.
The Scores Advantage: Time Energy & Cost Savings, 1 page, AmMed Surgical Equipment, LLC, date unknown.

MOBILE APPARATUS AND METHOD FOR STERILIZING ONE OR MORE SURGICAL TRAYS WITH INTEGRABLE TRANSFER AND STORAGE SYSTEM

CROSS-REFERENCE TO RELATED APPLICATIONS

This application is a continuation of U.S. patent application Ser. No. 16/212,579, filed on Dec. 6, 2018, which is a continuation of U.S. patent application Ser. No. 15/608,739, filed on May 30, 2017, now U.S. Pat. No. 10,179,183, which is a continuation of U.S. patent application Ser. No. 15/411,361, filed on Jan. 20, 2017, now U.S. Pat. No. 9,694,093, which is a continuation of U.S. patent application Ser. No. 13/944,875, filed on Jul. 17, 2013, now U.S. Pat. No. 9,616,143, the contents of each of which is incorporated herein by reference in its entirety.

BACKGROUND OF THE INVENTION

1. Field of the Invention

This invention relates to operating room sterilization equipment and methods, and in particular, to an improved mobile apparatus and method to sterilize one or more surgical trays, along with a dedicated integrable transfer and storage system.

2. Description of Related Art

A variety of instruments and supplies are required during modern operations. These are typically stored and sterilized in one or more wrapped trays. For example, an average knee replacement operation requires approximately twelve trays containing the instruments and supplies needed for this operation.

Traditionally, sterilization procedure has involved the steps of washing each tray, loading instruments and supplies into the tray, and then wrapping each tray individually within a protective wrap, frequently a 54-inch by 54-inch sterilizable linen or blue wrap. If a tray were to have sharp corners or protuberances, these would have to be padded with a towel or foam blocks to avoid tearing the protective wrap. The one or more loaded and wrapped trays would then be placed onto the shelves of a cart, and the cart inserted into an autoclave for sterilization.

Within the autoclave, the cart loaded with one or more trays generally would be sterilized at 270 degrees Fahrenheit for four to ten minutes, and then removed from the autoclave. The tray or trays are required to dry for up to 60 minutes before handling.

The tray or trays are put away into storage until needed. When required, each tray would be transported to the operating room, inspected and unwrapped as its contents were needed for the procedure being performed. Each tray would bear a chemical indicator that would read the sterilization status of a tray. Each chemical indicator would also then have to be inspected.

It would take in the vicinity of ten to fifteen minutes to inspect each tray and its chemical indicator and to unwrap the trays. Sterile 54-inch by 54-inch wraps cost approximately $3.00 per tray, so that a cart bearing twelve trays would require about $36.00 in sterile wraps. In addition, the cost of twelve chemical indicators and protective padding would have to be added to the sterilization costs for the cart.

If a wrap were found to have been torn or breached, the contents of the tray to which that wrap had been applied would have to be considered non-sterile. In this event, the autoclaving procedure would have to be repeated (which takes about one hour and 45 minutes), or in the alternative, an emergency "flash autoclave" would have to be performed. A flash autoclave involves sterilizing a tray in an autoclave for about ten minutes. A flash autoclave is not as thorough a sterilization as the full procedure, and carries greater risks. Therefore, when a sterile wrap was discovered to have been torn or breached in the operating room while a procedure was underway, the surgeon would be faced with the undesirable choice of having to wait one hour and 45 minutes for a full autoclave sterilization, or order a flash autoclave if such a delay were unacceptable. Any delay could be potentially damaging to the patient, because time spent under anesthesia is best minimized.

Mobile Apparatus and Method to Sterilize Surgical Trays, U.S. Pat. No. 8,454,901 (Snyder) teaches a mobile apparatus and method to sterilize surgical trays which does not require the use of protective wraps, which reduces the number of chemical indicators required, and which contemplates the capacity to transport the sterilization apparatus to and from an autoclave, a storage area, or an operating room. This apparatus and method, however, while clearly superior to more traditional sterilization processes, still requires the use of a large industrial autoclave, and provides adequate no means for readily moving the apparatus between a sterilization location, a storage area, and an operating room.

The large industrial autoclaves used in hospitals are very expensive pieces of equipment, costing between $100,000.00 and $250,000.00 each. A big hospital typically may have between four and six such autoclaves, which constitute a substantial capital investment. Moreover, there are other significant operational costs associated with these autoclaves, including labor and material costs associated with the preparation for each sterilization, as well as ongoing maintenance and repair. The failure of even a single autoclave can result in not only additional economic outlays, but in potentially adverse consequences for patient care.

By eliminating the need for separate industrial-sized autoclaves, a medical facility could enjoy substantial capital and operational savings, and patient care could be enhanced and rendered more reliable. Storage space could be better utilized and more sterilizations could be carried out in less time, particularly if a compact autoclave apparatus were to be integrated with a means of easily and securely transporting it from one location to another and with a means of maximizing the ease and efficiency with which such an apparatus were to be stored.

BRIEF SUMMARY OF THE INVENTION

The present invention, an improved mobile apparatus and method to sterilize surgical trays, comprises a cabinet, at least one shelf sized to support one or more surgical trays, and removable, autoclavable wheels. Surgical trays are placed within the cabinet, the cabinet doors are closed, and to sterilize the trays, an effective quantity of a sterilization agent is introduced into the cabinet via one or more input couplers attached to the cabinet for a time sufficient to carry out the sterilization of the interior of the cabinet and any contents thereof. The sterilization agent may then be removed from the cabinet via one or more vacuum outlet couplers. The cabinet doors are not unsealed until the cabinet is in the operating room, ready for use. At that point the doors may be opened, any trays removed, and the sterilized contents of the trays used.

Chemical indicators and a locator card may be used to verify the sterilization status and autoclave history of the cabinet and its contents. Maintenance steps include periodically replacing the filters and door gasket. In at least one embodiment of the invention, the cabinet may be configured readily into a surgical back table. RF location software and hardware may be incorporated into the apparatus as well.

The invention further comprises and integrable transfer and storage system that includes a transfer cart to facilitate moving the cabinet between storage areas, operating rooms, and other locations within a medical facility, as well as a modular lift device allowing the cabinets to be stacked vertically for maximum storage efficiency. A transfer cart may also be stored within the lift device.

REFERENCE NUMERALS IN THE DRAWINGS

Figure 1:
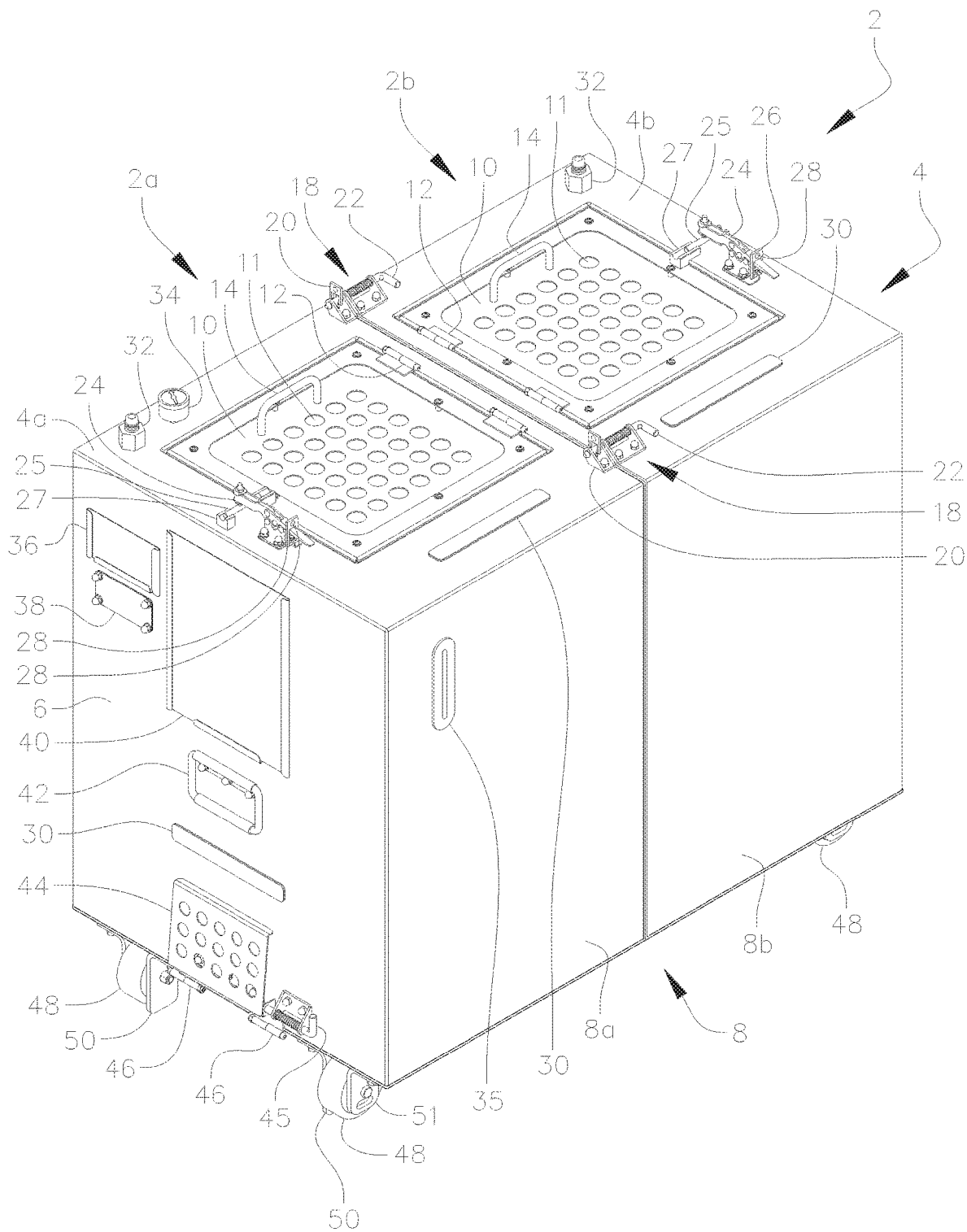
FIG. 1 is a front left top isometric view of a clamshell-style embodiment of a Cabinet 2 with two closed Filter Well Vented Doors 10 on a Cabinet Roof 4 comprised of a Left Cabinet Roof 4a and a the Right Cabinet Roof 4b.

2 Cabinet
2a Cabinet Left Portion
2b Cabinet Right Portion
4 Cabinet Roof
4a Cabinet Left Roof
4b Cabinet Right Roof
6 Cabinet Left Side
7 Cabinet Right Side
8 Cabinet Front
8a Cabinet Front Left Side
8b Cabinet Front Right Side
9 Cabinet Back
9a Cabinet Back Left Side
9b Cabinet Back Right Side
10 Filter Well Vented Door
11 Vent Hole
12 Filter Well Vented Door Hinge
14 Filter Well Vented Door Handle
16 Cabinet Floor
18 Clamshell Closure
20 Clamshell Closure—Female Member
22 Clamshell Closure—Male Member
24 Filter Well Vent Door Cam-Lock
25 Filter Well Vent Door Cam-Lock Male Element
26 Closure Integrity Lock
27 Filter Well Vent Door Cam-Lock Female Element
28 Chemical Indicator Sticker
30 FDA Certification Placard
32 Inlet Coupler
34 Pressure Gauge
35 Temperature Gauge
36 Chemical Indicator Card Holder
38 Serial/Lot Code Data Plate
40 Locator Card Holder
42 Cabinet Handle
44 External Cabinet Shelf
45 External Cabinet Shelf Lock
46 Clamshell Hinge 48 Cabinet Wheel
50 Long Safety Retention Tab
51 Short Safety Retention Tab With Slot
52 Bar Code Indicator
53 Cabinet Stabilization Rod Bracket
54 Filter Well Vented Door Gasket
56 Filter
58 Filter Well
58a Left Bottom Filter Well
58b Right Bottom Filter Well
60 Cabinet Bottom
62 Outlet Coupler
64 Clamshell Gasket
66 Shelf
67 Cabinet Interior Back
68 Cabinet Back Right—Inside Wall
70 Cabinet Interior Right Side
72 Cabinet Side—Right
74 Cabinet Back Left—Inside Wall
76 Cabinet Side—Inside Left
78 Cabinet Ceiling
79 Shelf Support
80 Shelf Support Aperture
81 Transfer Cart
82 Transfer Cart Lower Assembly
83 Transfer Cart Upper Assembly
84 Transfer Cart Dock
85 Cabinet Safety Pin
86 Transfer Cart Connecting Rail
87 Transfer Cart Leveler
88 Transfer Cart Handle
89 Transfer Cart Shelf
90 Transfer Cart Integrated Autoclave Locking Mechanism
91 Transfer Cart Frame
92 Transfer Cart Integrated Cabinet Locking Mechanism
93 Transfer Cart Solid Shelf
94 Transfer Cart Stabilization Rod
95 Cabinet Safety Lock
96 Transfer Cart Wheel
97 Autoclave Disengaging Rod
98 Transfer Cart Wheel Lock
99 Autoclave Disengaging Rod Collar
100 Lift Device
101 Autoclave Disengaging Rod Spring
102 Lift Device Control Panel
103 Autoclave Disengaging Rod Handle
104 Lift Device Wheel Assembly
105 Autoclave Locking Hook
106 Cabinet Safety Lock Handle
107 Lift Channel
108 Plate
109 Lift Rail
110 Lift Dock
111 Lift Support Bar
113 Safety Retention Bar
115 Modular Connection Caps
117 Lift Device Frame
118 Transfer Cart Wheel Assembly
119 Transfer Cart Serial Number Plate
120 Cabinet Door
121 Lift Device Frame Base Plate
122 Cabinet Door Handle
123 Cabinet Door Catch
124 Cabinet Door Closure
126 Cabinet Door Hinge
130 Cabinet Door Gasket
132 Left Cabinet Door
134 Right Cabinet Door
136 Cabinet Door Closure Female Element
138 Cabinet Door Closure Male Element
140 Cabinet Aperture
142 Interior Cabinet Face
150 Lift Wheel
152 Lift Wheel Lock
160 Cabinet Interior Face
162 Cabinet Exterior Face

DETAILED DESCRIPTION OF THE INVENTION

The present invention is an improvement over, and may incorporate all or any combination of features found in U.S. Pat. No. 8,454,901 B1 (Snyder). The invention that is the subject of the instant application comprises a Cabinet 2, integrable with a Transfer Cart 81 and Lift Device 100, having cabinet access means for opening and closing the Cabinet 2, cabinet securing means to maintain a Cabinet 2 in a closed state, as well as at least one Shelf 66 capable of admitting at least one surgical tray. The term 'cabinet access means' as utilized herein is intended to include any structure that can be employed to carry out the function of opening and closing a Cabinet 2, and the term 'cabinet securing means' is intended to include any structure that can be employed to carry out the function of fastening to ensure that a Cabinet 2 remains in a closed state, whether or not such a structure is recited with particularity herein.

A Cabinet 2, which may be made from stainless steel, other metal or synthetic materials, or indeed, any other suitable materials or combinations of any such suitable materials whatsoever, may have one or more filterable vents allowing air to pass between the exterior to the interior of the Cabinet 2, said vents typically located in the vicinity of a Cabinet Roof 4, a Cabinet Bottom 60, or both. After at least one standard surgical tray has been loaded into a Cabinet 2 and the Cabinet 2 has been closed and sealed, steam, ethylene oxide gas (ETO) or any other appropriate sterilization agent is introduced into the Cabinet 2 through at least one Input Coupler 32 in an effective amount for a time sufficient to achieve sterilization of the interior of the Cabinet 2 and its contents.

A sterilization agent thereafter may be evacuated from a Cabinet 2 through at least one vacuum Outlet Coupler 62, and the Cabinet 2 then may transferred a storage area until needed or otherwise be taken to an operating room where the Cabinet 2 may be reopened and unsealed, and any surgical tray therein removed and used as required, obviating the necessity of protective wraps and redundant chemical indicators, as well as the necessity of an industrial autoclave into which the entire Cabinet 2 must be inserted in order to carry out sterilization of the interior of the Cabinet 2 and its contents.

The Cabinet 2 has been designed to be integrated with a Transfer Cart 81 and transported via said Transfer Cart 81 between a given sterilization location, a storage location, and an operating room. A Transfer Cart 81 itself is designed to be secured to an industrial autoclave for purposes of transferring a Cabinet 2 from the Transport Cart 81 into an industrial autoclave, if desired, for sterilization of an entire Cabinet 2 and its contents. The Cabinet 2 and the Transfer Cart 81 are meant to integrate with a dedicated modular, expandable Lift Device 100 that allows vertical stacking of Cabinets 2 for efficient storage and provides a means of storage for at least one Transfer Cart 81 as well.

FIG. 1 is a front left top isometric view of a clamshell-style embodiment of a Cabinet 2 in a closed state. In this embodiment, the Cabinet 2 comprises a Left Cabinet Portion 2a and a Right Cabinet Portion 2b. Clamshell Hinges 46 allow the Cabinet 2 to be opened and reopened to access the interior of the Cabinet 2 by pivotally rotating the Left Cabinet Portion 2a and the Right Cabinet Portion 2b independently away from one another, and closed and reclosed by pivotally rotating said portions towards one another. The Left Cabinet Portion 2a and the Right Cabinet Portion 2b may secured together in the closed state by any cabinet securing means, which will typically be mechanical in nature, such as the Clamshell Closures 18 illustrated in FIG. 1, each such Clamshell Closure 18 comprising a Clamshell Closure Female Member 20 and a Clamshell Closure Male Member 22.

In this particular clamshell-style embodiment, a Cabinet Roof 4 is formed by a Left Cabinet Roof 4a and a Right Cabinet Roof 4b adjacent to one another when the clamshell embodiment of the Cabinet 2 is in a closed state. One or more Filter Well Vented Doors 10, each of which may include a Filter Well Vented Door Handle 14, may be located on both the Left Cabinet Roof 4a and the Right Cabinet Roof 4b. Every Filter Well Vented Door 10 has a plurality of Vent Holes 11. Each Filter Well Vented Door 10 may be removably attached to the Cabinet Roof 4 or Cabinet Floor 16 (see FIG. 8) by means of a Filter Well Vented Door Hinge 12, and each Filter Well Vented Door 10 may employ a Filter Well Vented Door Handle 14 to facilitate the opening and closing of the Filter Well Vented Door 10.

A Filter Well Vented Door 10 may be secured in a closed position by locking means, such as the Filter Well Vent Door Cam-Lock 24 pictured in the embodiment in FIG. 1. A Filter Well Vent Door Cam-Lock 24 typically may be comprised of one or more Filter Well Vent Door Cam-Lock Female Elements 27 and one or more Filter Well Vent Door Cam-Lock Male Elements 25. Security integrity means, typically mechanical in nature, such as the Closure Integrity Lock 26 illustrated, may be used to ensure the integrity of any locking means, such as a Filter Well Vent Door Cam-Lock 24, so that said cabinet securing means do not become disengaged or otherwise fail during the course of sterilization. The term 'security integrity means' is intended to include any structure that can be employed to carry out the function of ensuring or enhancing the integrity of any other securing means or locking means, whether or not such a structure is recited with particularity herein. A Chemical Indicator Sticker 28 may be applied to any Closure Integrity Lock 26 to help to ascertain readily the sterilization status of the Cabinet 2.

As illustrated in the embodiment present in FIG. 1, a Pressure Gauge 34 and a Temperature Gauge 35 may be incorporated into the Cabinet 2 to allow monitoring of the temperature and pressure on the inside of the Cabinet 2 before, during, and after sterilization. A Chemical Indicator Card Holder 36 in which a chemical indicator card (not illustrated) may be inserted to further ascertain the sterilization status of the Cabinet 2 also may be positioned on the outside of the Cabinet 2. A Serial/Lot Code Data Plate 38 can be attached to the Cabinet 2 for identifying the Cabinet 2, and a Locator Card Holder 40 may be included on the Cabinet 2 to accept a locator card (not illustrated) for recording the history of the Cabinet 2, e.g., the date and time that the Cabinet 2 has undergone autoclave. FDA Certification Placards 30 may provide information required by federal law and regulations concerning requirements and recommendations respecting the Cabinet 2 and its operation.

Each Cabinet 2 may have a plurality of removable, autoclavable Cabinet Wheels 48 to facilitate its movement between a dedicated Transfer Cart 81 with one or more Transfer Cart Connecting Rails 86 and a designated Lift Device 100 with one or more Lift Rails 109. A Cabinet Wheel 48, together with a Long Safety Retention Tab 50 and a Short Safety Retention Tab with Slot 51, may be attached to a Cabinet 2 by screws or by any other suitable attachment means. The Long Safety Retention Tab 50 associated with a Cabinet Wheel 48 serves to keep the Cabinet Wheel 48 on and guided by a Transfer Cart Connecting Rail 86, a Lift Rail 109, or a rail used in an industrial autoclave, as well as to provide a structure with which a Cabinet Safety Lock 95 may engage to secure a Cabinet 2 to a Transfer Cart 81. The Short Safety Retention Tab with Slot 51 associated with a Cabinet Wheel 48 provides a structure with which a Cabinet Safety Pin 85 may engage to secure a Cabinet 2 to a Transfer Cart 81.

FIG. 1 further reflects a Cabinet Handle 42 on a Cabinet Right Side 6. A Cabinet Handle 42 may be positioned on either side of the Cabinet 2 to allow the Cabinet 2 to be pulled or otherwise manipulated into a desired position. The Cabinet may also have a hinged deployable External Cabinet Shelf 44 for the placement of a biological challenge pack for orthopedic prostheses and similar items, which may be sterilized within the Cabinet 2. The External Cabinet Shelf 44 may be locked into place and unlocked by means of an External Cabinwet Shelf Lock 45.

Figure 2:
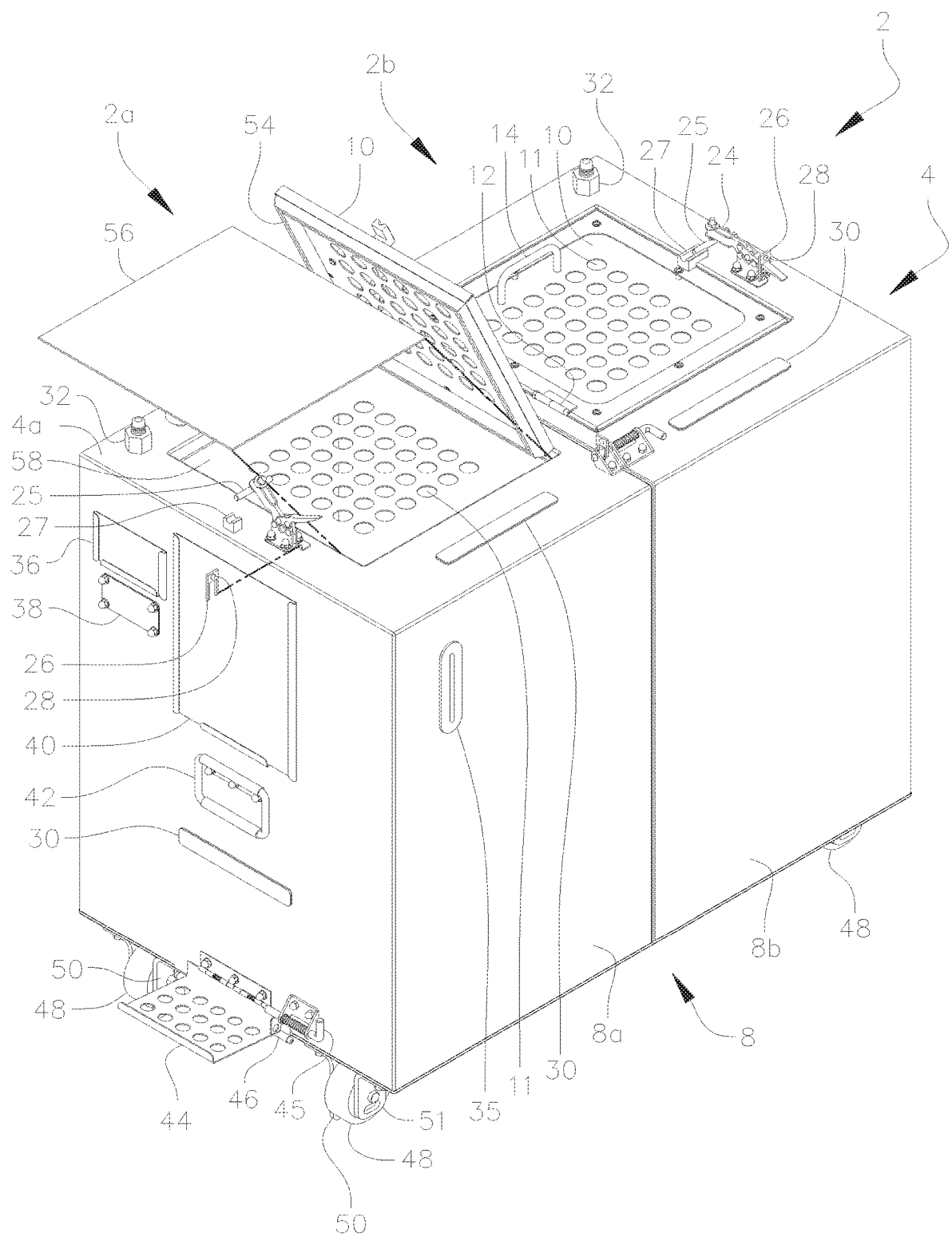
FIG. 2 is a front left top isometric view of a clamshell-style embodiment of a Cabinet 2 with two Filter Well Vented Doors 10 on the Cabinet Roof 4, the one on the Left Cabinet Roof 4a being open to reveal a Filter Well 58 underneath into which a Filter 56 may be inserted.

FIG. 2 is another front left top isometric view of a clamshell-style embodiment of the Cabinet 2 in a closed state, but with a Filter Well Vented Door Cam-Lock 24 disengaged and Closure Integrity Lock 26 removed, and an associated Filter Well Vented Door 10 opened to reveal a Filter Well 58 in a Left Cabinet Roof 4a into which a Filter 56, typically made of paper, fabric, synthetic, or other appropriate material or combination of materials, may be inserted and subsequently held in place when the Filter Well Vented Door 10 is closed and secured with the Filter Well Vented Door Cam-Lock 24. Each Filter Well 58 has a plurality of Vent Holes 11. The Filter Well Vented Door 10 employs a Filter Well Vented Door Gasket 54 intended to create an airtight seal with the Filter Well 58. Thus, air may pass between the exterior and the interior of the Cabinet 2 through the Vent Holes 11 in the Filter Well 58, the Filter 56, and the Vent Holes 11 in the Filter Well Vented Door 10 when a Filter 56 is interposed between the Filter Well 58 and the Filter Well Vented Door 10, but may not circumvent the Filter 56. FIG. 2 additionally illustrates the External Cabinet Shelf 44 in a fully deployed position.

Figure 3:
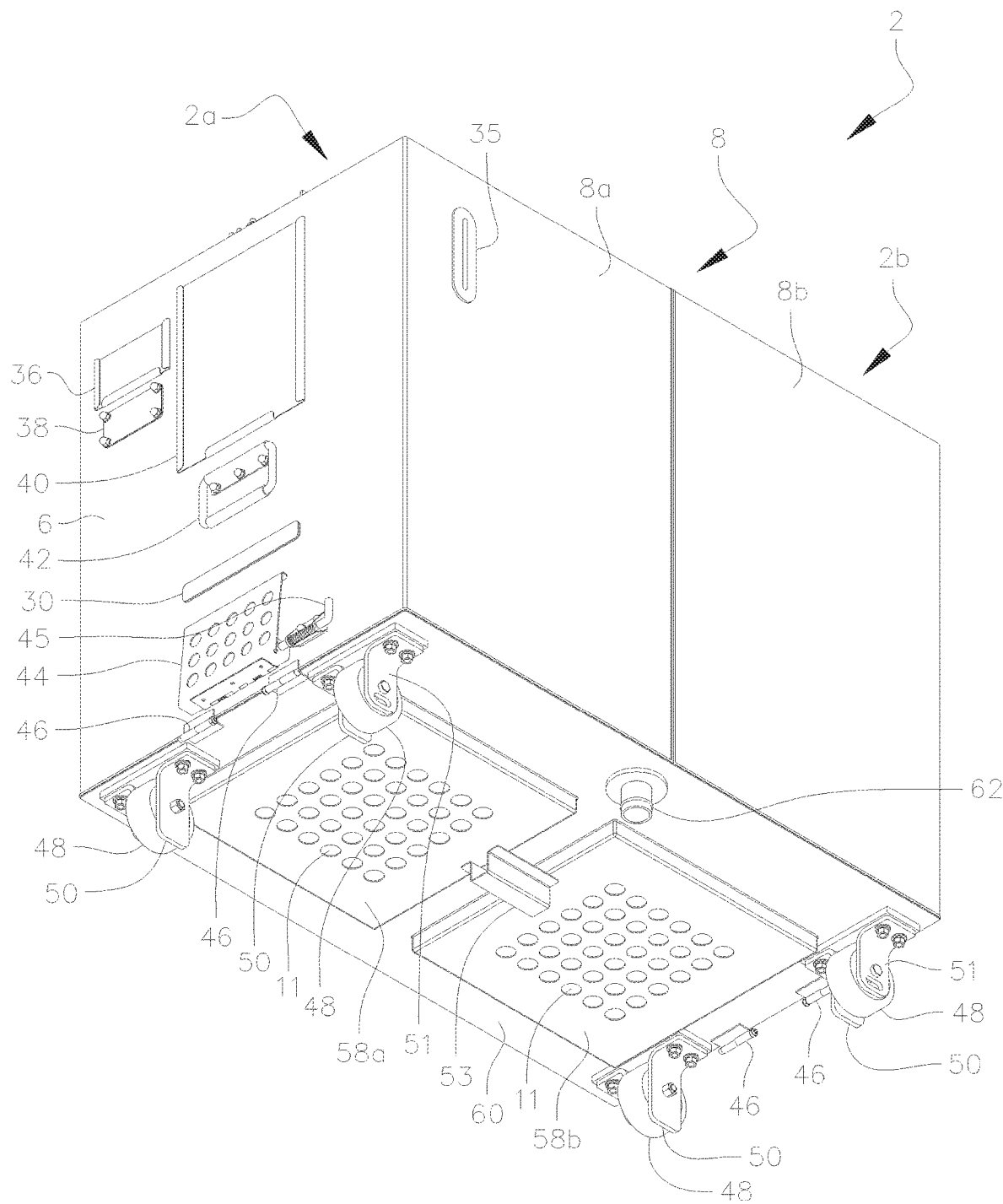
FIG. 3 is a front left bottom isometric view of a clamshell-style embodiment of a Cabinet 2 illustrating details of the Cabinet Bottom 60, including Left Bottom Filter Well 58a and Right Bottom Filter Well 58b.

FIG. 3 is a front left bottom isometric view of the Cabinet 2 revealing several features in the area of a vented Cabinet Bottom 60. A Cabinet Bottom 60 may have at least one Filter Well 58. In the embodiment illustrated in FIG. 3, there is Left Bottom Filter Well 58a and a Right Bottom Filter Well 58b, each of which has Vent Holes 11. A Cabinet Stabilization Rod Bracket 53, which may be located on or about the Cabinet Bottom 60, is shown in FIG. 3 to be positioned longitudinally across a center portion of the Left Bottom Filter Well 58a and the Right Bottom Filter Well 58b. Any sterilization agent introduced into the Cabinet 2 may be extracted through an Outlet Coupler 62. FIG. 3 shows how the Long Safety Retention Tab 50 may extend below the Cabinet Wheel 48, and also illustrates in greater detail the Short Safety Retention Tab with Slot 51.

Figure 4:
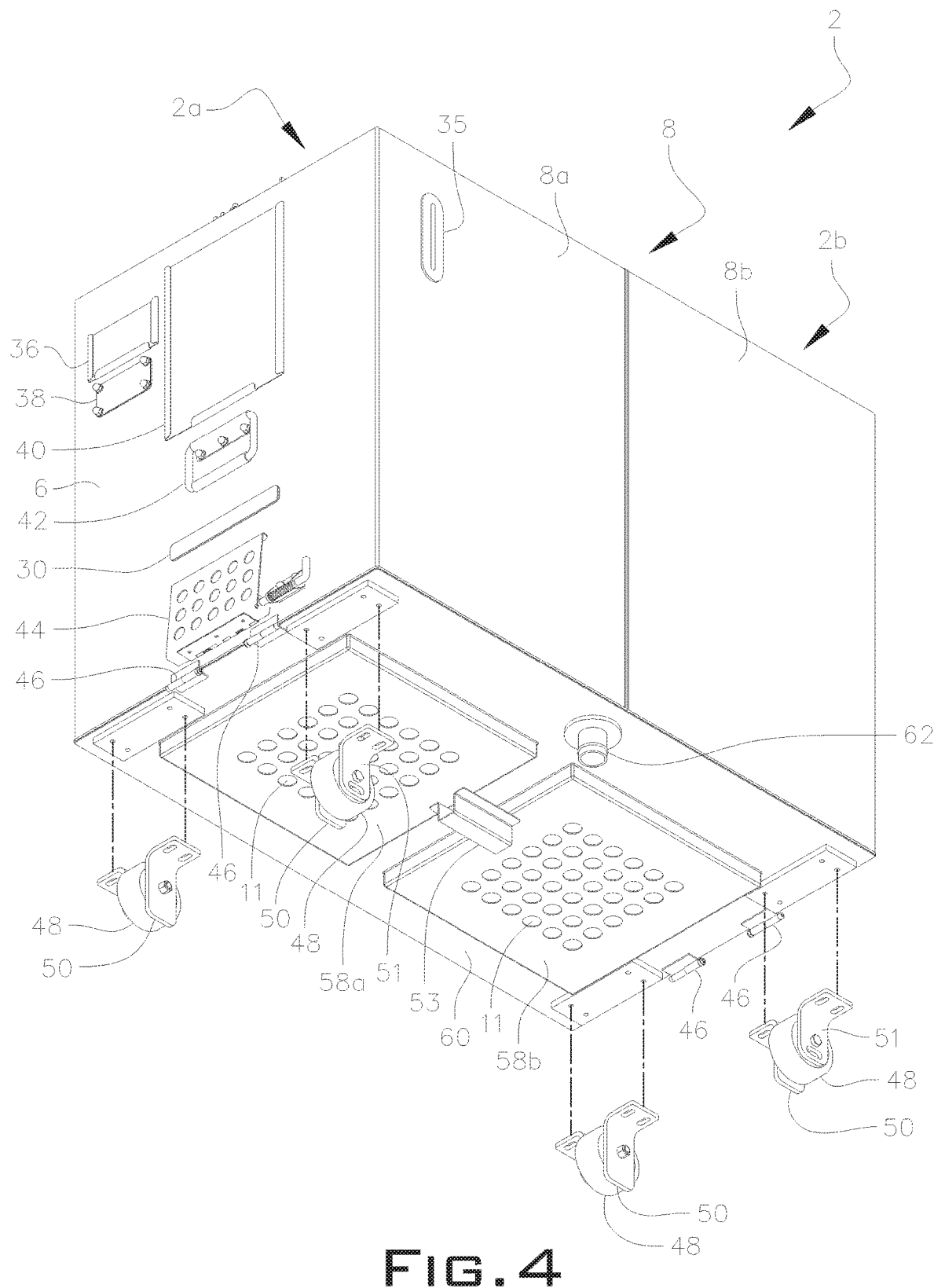
FIG. 4 is a front left bottom isometric view of a clamshell-style embodiment of a Cabinet 2 reflecting the removable character of each Cabinet Wheel 48 and its associated Long Safety Retention Tab 50 and Short Safety Retention Tab with Slot 51.

FIG. 4 presents another front left bottom isometric view of the Cabinet 2. Each removable Cabinet Wheel 48 may be attached to the Cabinet Bottom 60 by way of screws or other suitable attachment means. The removable character of each Cabinet Wheel 48 in this particular embodiment is clearly illustrated.

Figure 5:
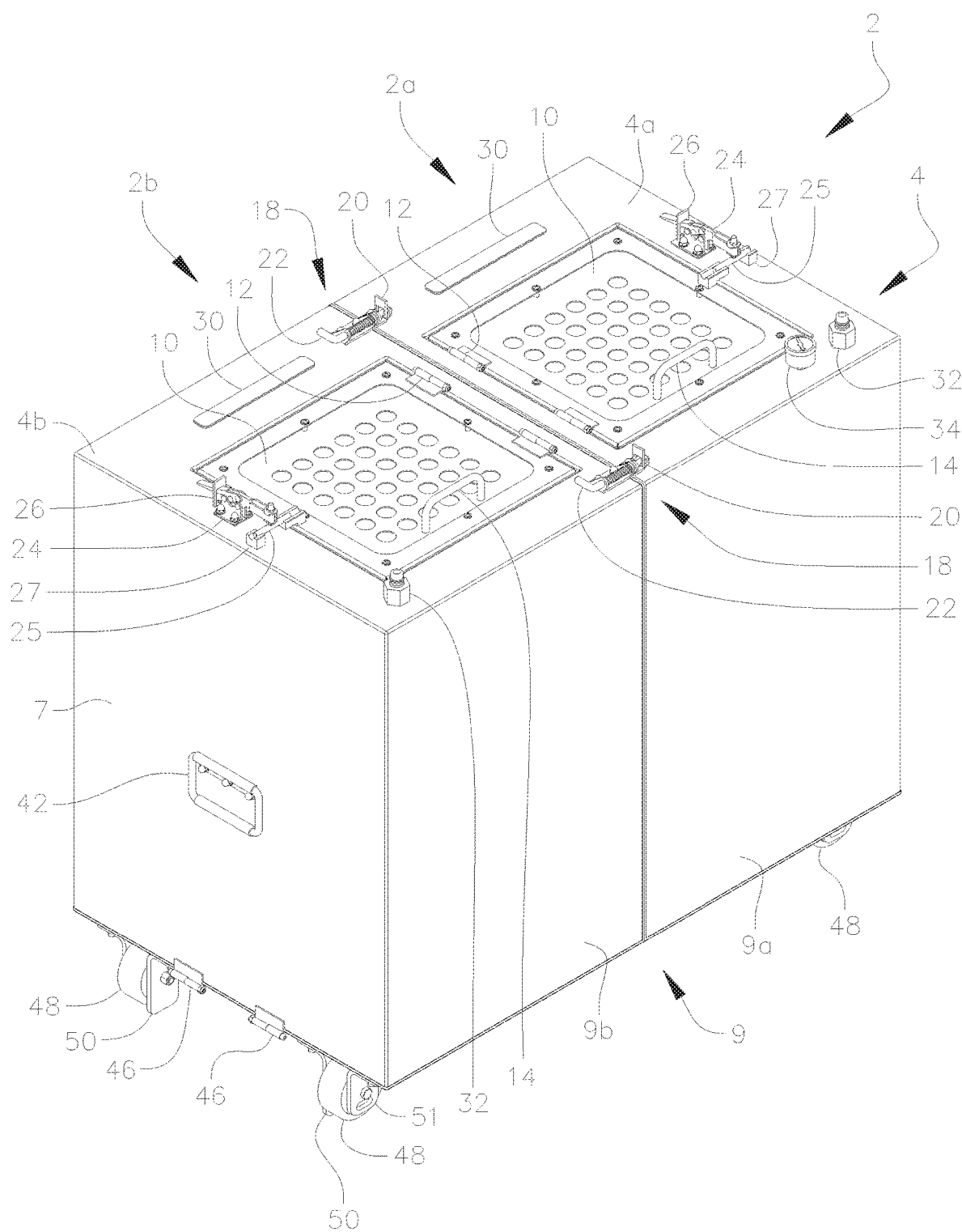
FIG. 5 is a back left top isometric view of a clamshell-style embodiment of a Cabinet 2.

A back right top view of a Cabinet 2 is presented in FIG. 5.

Figure 6:
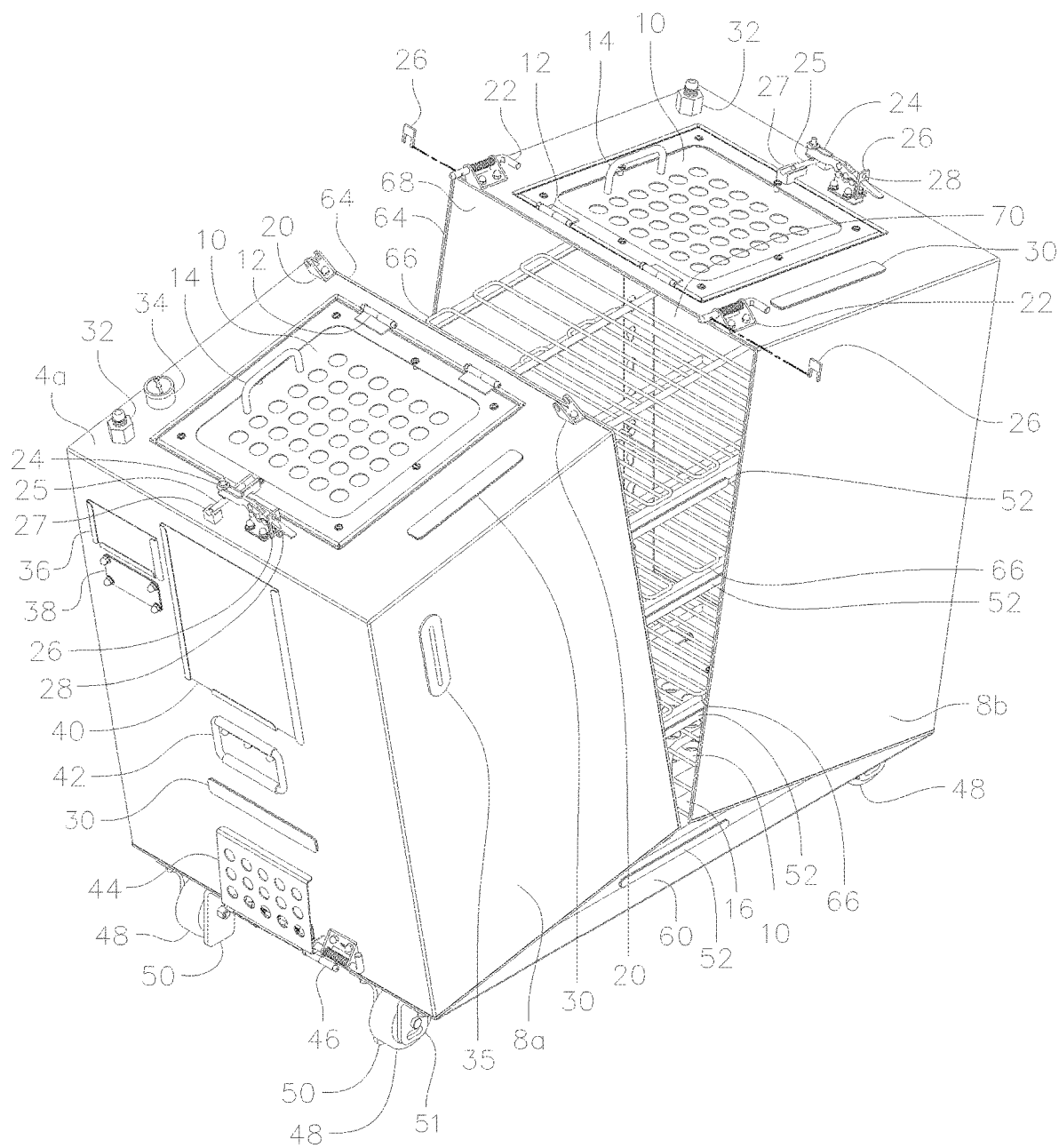
FIG. 6 is a front left top isometric view presenting a clamshell-style embodiment of a Cabinet 2 in a partially open state.

In FIG. 6, a clamshell-style embodiment of a Cabinet 2 is illustrated in a partially open state, in which a Left Cabinet Portion 2a and a Right Cabinet Portion have been partially pivotally rotated away from one another. When the Cabinet 2 is in a closed state, each Clamshell Gasket 64, which may be made of heat-resistant silicone or other suitable material, creates a seal between the Left Cabinet Portion 2a and the Right Cabinet Portion 2b, as well as between the Left Cabinet Portion 2a and the Cabinet Floor 60 and between the Right Cabinet Portion 2b and the Cabinet Floor 60. The one or more Shelves 66 within the Cabinet 2 serve to accept and support one or more surgical trays inside the Cabinet 2. Each Shelf 66 placed within the Cabinet 2 may have its own Bar Code Indicator 52 for identification purposes.

Figure 7:
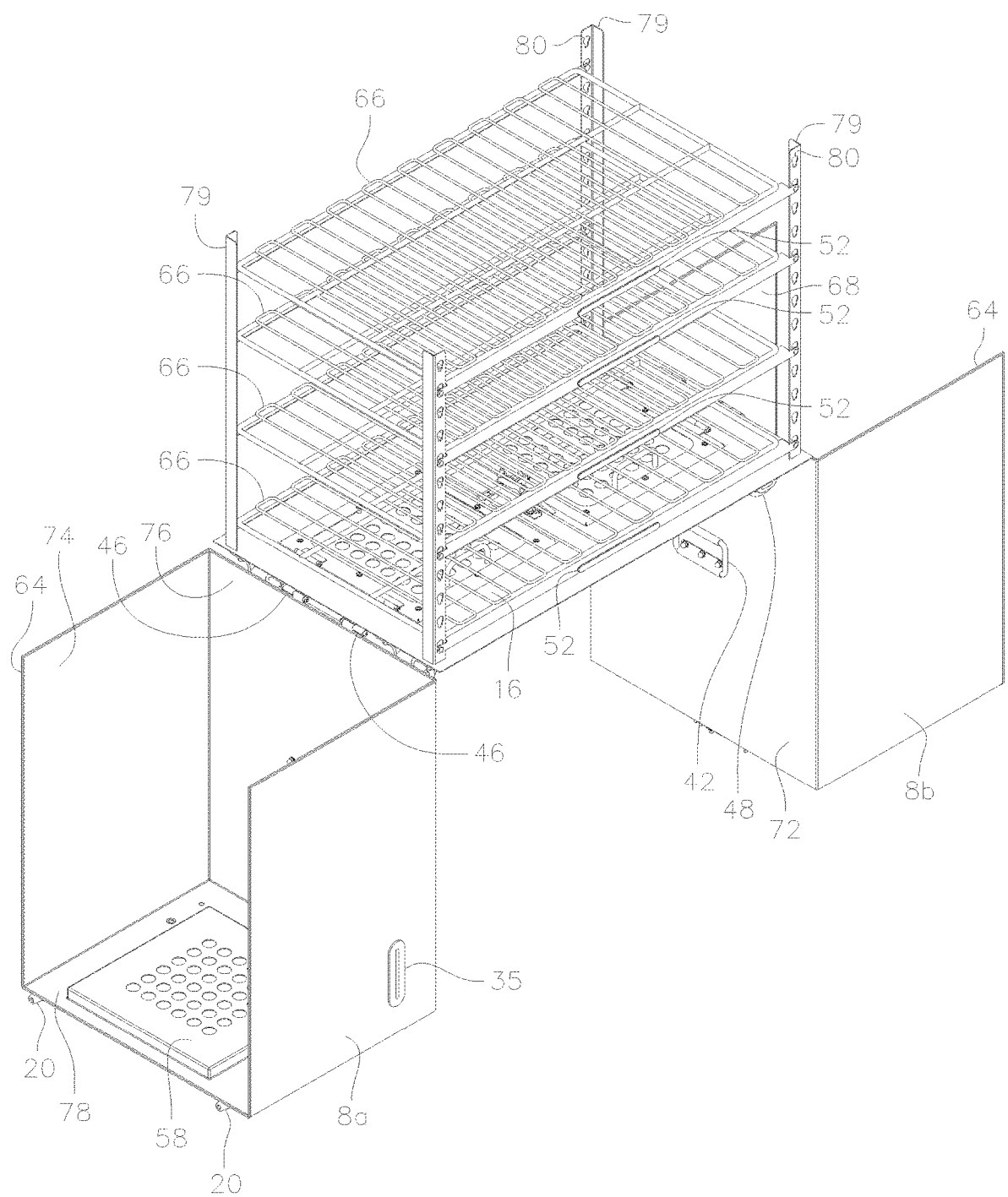
FIG. 7 is a front left top isometric view showing a clamshell-style embodiment of a Cabinet 2 in a fully open state for use as a surgical back table, with a plurality of Shelves 66 supported by a plurality of Shelf Supports 79.

FIG. 7 illustrates the ability of the particular clamshell-style embodiment depicted to be configured as a surgical back table by pivotally rotating the Left Cabinet Portion 2a and the Right Cabinet Portion 2b into a fully open position allowing the Left Cabinet Roof 4a and the Right Cabinet Roof 4b to rest on the floor. FIG. 7 additionally reveals a plurality of vertically disposed Shelf Supports 79 within the Cabinet 2 when it is in a closed state that are together capable of supporting each Shelf 66 within the Cabinet 2. Each Shelf 66 may be removably coupled or otherwise attached to each Shelf Support 79. In the illustrated embodiment, this is accomplished by means of attaching a Shelf 66 to a Shelf Support 79 via a plurality of Shelf Support Apertures 80 associated with each Shelf Support 79. The level of each Shelf 66 relative to the vertically disposed Shelf Supports 79 may be adjusted by attaching a Shelf 66 to different sets of Shelf Support Apertures 80 at the same level.

Figure 8:
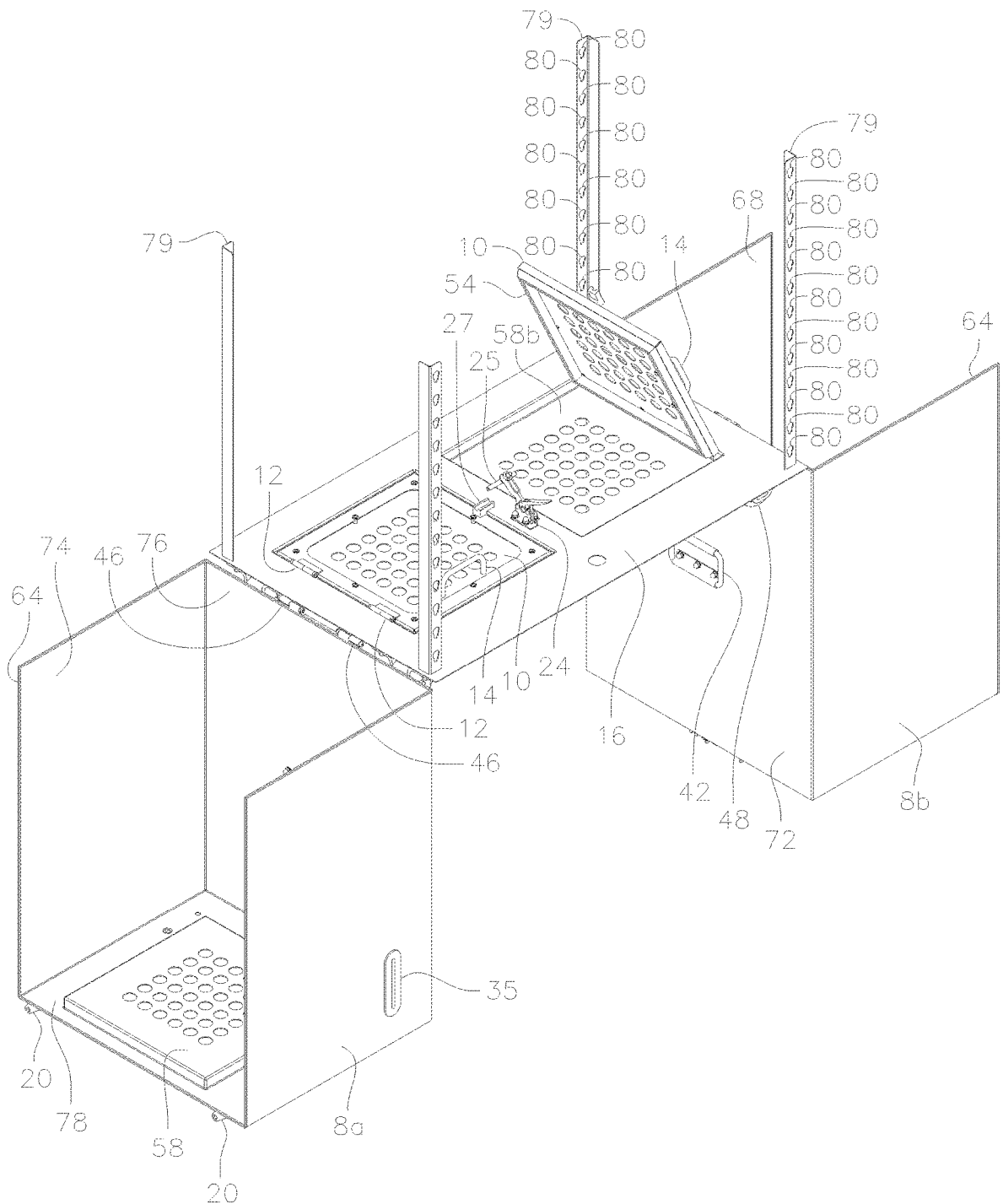
FIG. 8 is a front left top isometric view presenting a clamshell-style embodiment of a Cabinet 2 in a fully open state revealing two Filter Well Vented Doors 10 on the Cabinet Floor 16, one in an open state, a single open Filter Well Vent Door Cam-Lock 24 used to secure them both, and a Filter Well 58b exposed by the open Filter Well Vented Door 10.

FIG. 8 illustrates the location of a Filter Well Vent Door 10 located on the Cabinet Floor 16, including a Filter Well Vent Door 10 in an open position to reveal a Filter Well 58 below, said Filter Well 58 being the Right Bottom Filter Well 58b of FIG. 3 and FIG. 4.

Figure 17:
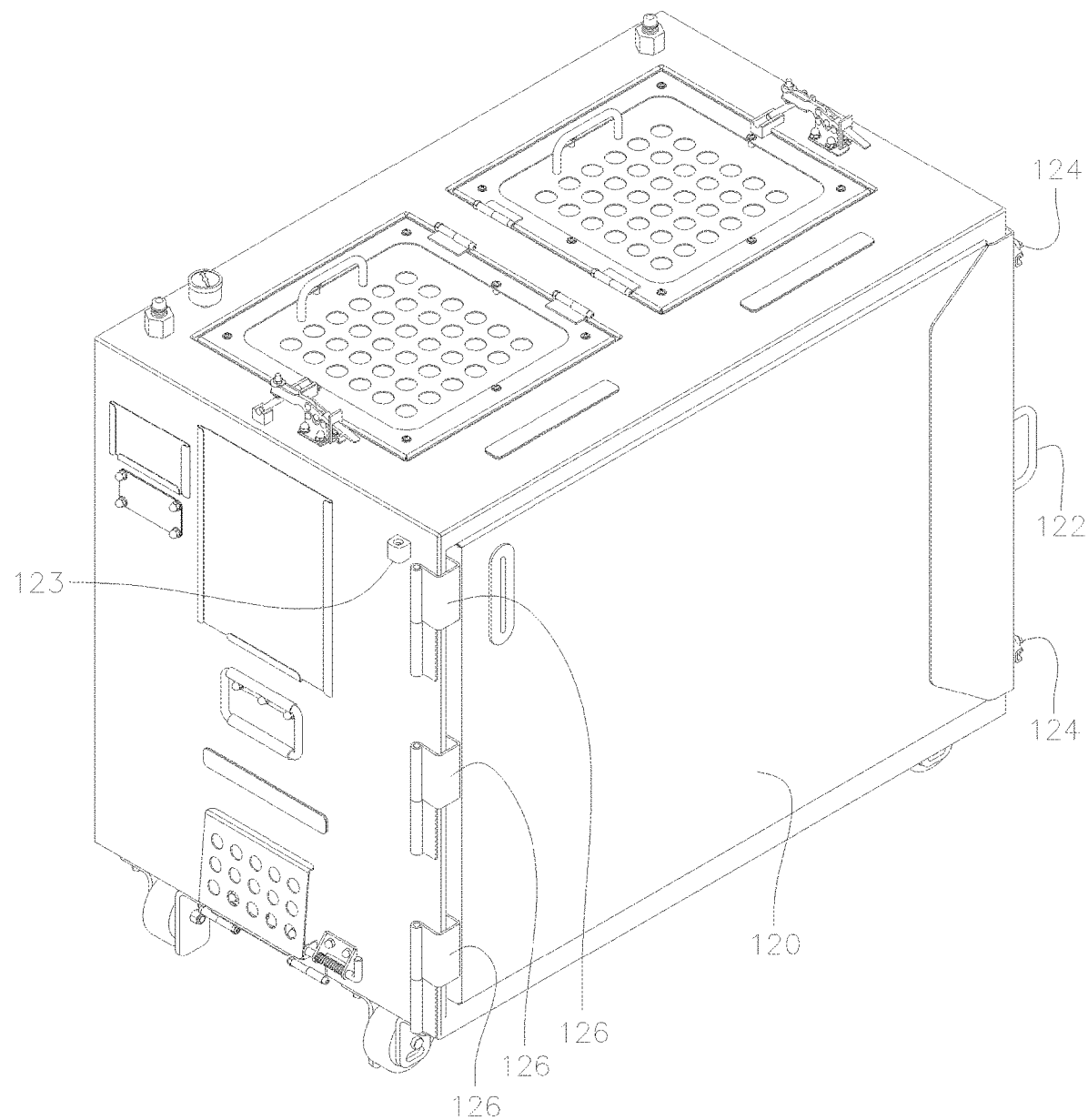
FIG. 17 is a front left top isometric view of a particular embodiment of a Cabinet 2 with a single Cabinet Door 120 in a closed position.

FIG. 17 depicts an alternative embodiment of a Cabinet 2 with a single Cabinet Door 120, hingeably connected to the Cabinet 2 via a plurality of Cabinet Door Hinges 126 on the Cabinet Left Side 6. Alternatively, a single Cabinet Door Hinge 126 may be used to hingeably connect a Cabinet Door 120 to a Cabinet 2. A Cabinet Door Handle 122 may be utilized to facilitate opening and closing a Cabinet Door 120. A Cabinet Door Catch 123 proximate to a Cabinet Door Hinge 126 allows the Cabinet Door to be held in the open position when loading or unloading a Cabinet 2. One or more cabinet securing means, such as the Cabinet Door Closures 124 illustrated, may be employed to fasten a Cabinet Door 120 to a Cabinet 2 to maintain a Cabinet 2 in a closed state.

Figure 18:
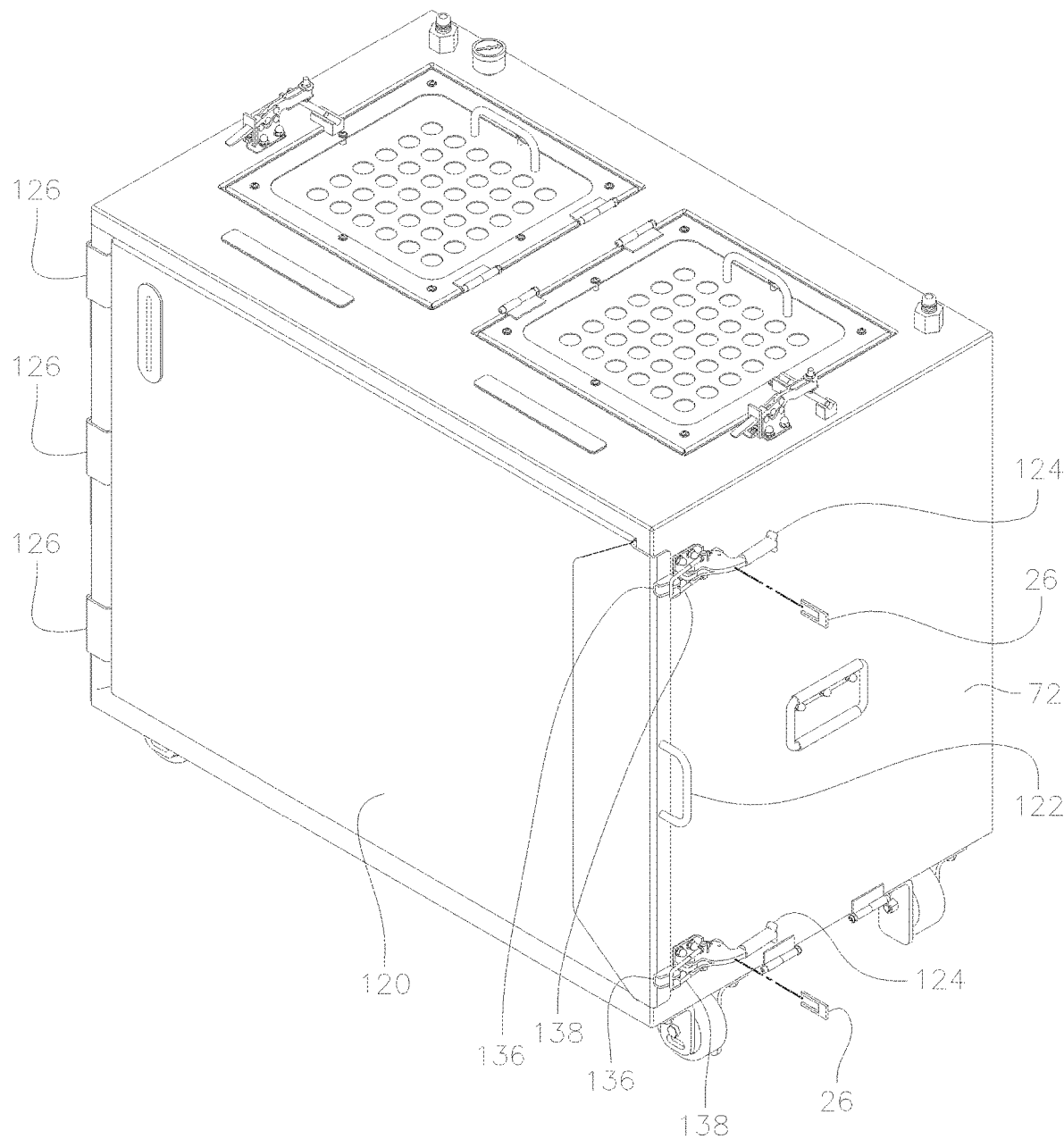
FIG. 18 is a front right top isometric view of a particular embodiment of a Cabinet 2 with a single Cabinet Door 120 in a closed position.

In the particular embodiment of the Cabinet 2 that appears in FIG. 18, each Cabinet Door Closure 124 comprises a Cabinet Door Closure Female Element 136 attached to a Cabinet Door 120 and a Cabinet Door Closure Male Element 138 attached to a Cabinet 2 on the Cabinet Right Side 7. Security integrity means such as a Closure Integrity Lock 26 may be employed to ensure that a Cabinet Door Closure 124 remains engaged or otherwise does not fail throughout any sterilization process.

Figure 19:
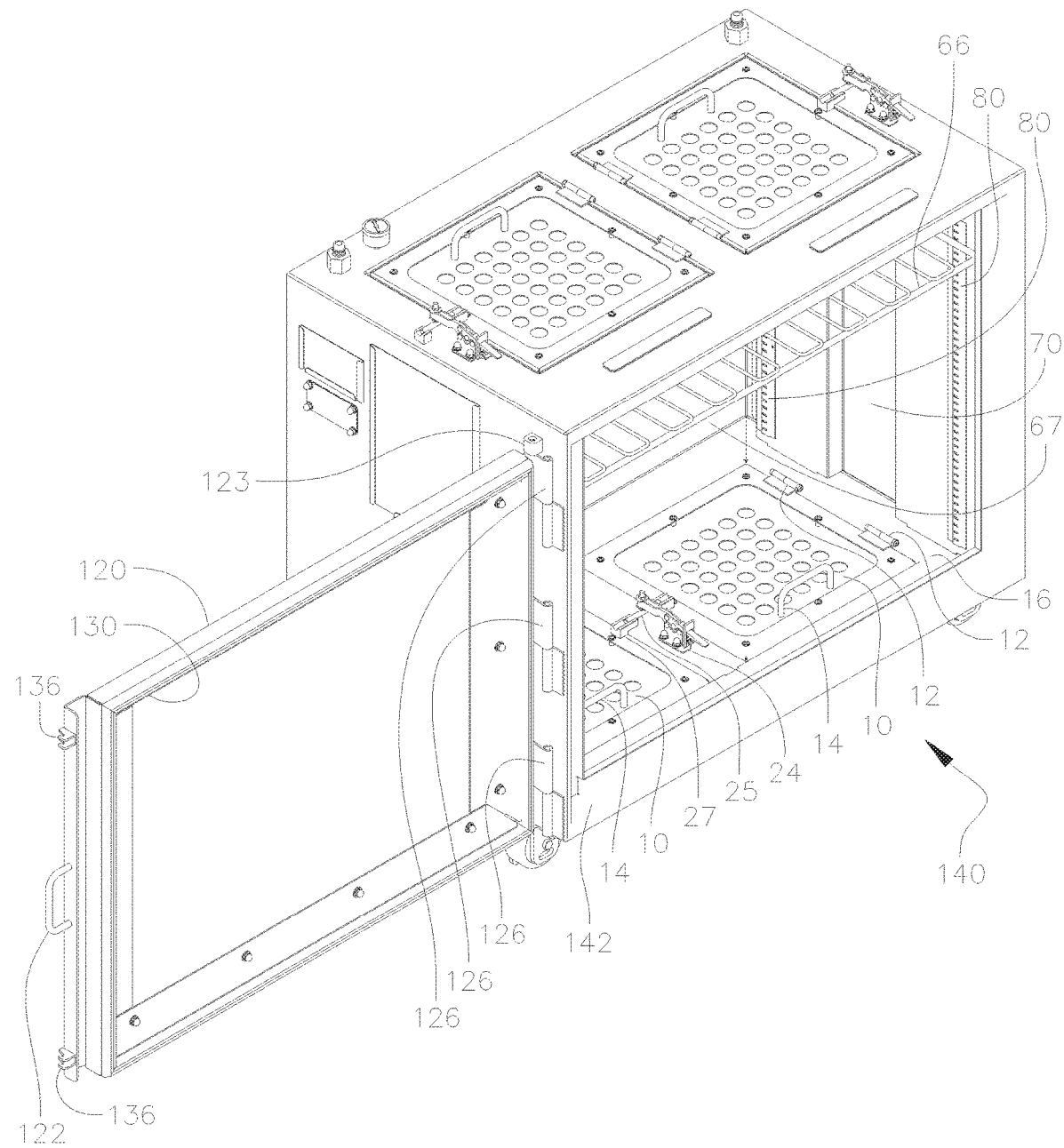
FIG. 19 is a front left top isometric view of a particular embodiment of a Cabinet 2 with a single Cabinet Door 120 in an open position.

FIG. 19 illustrates an embodiment of a Cabinet 2 with a single Cabinet Door 120 in the fully open position with a Cabinet Door Catch 123 engaged. The Cabinet Interior Right Side 70, Cabinet Interior Back 67, and Cabinet Floor 16 are revealed. In this particular embodiment of the Cabinet 2, two Shelf Supports 79 are fixed to the Cabinet Interior Right Side 70 and to the opposite facing interior side (not visible in this view). The level of each Shelf 66 relative to the vertically disposed Shelf Supports 79 may be adjusted by attaching a Shelf 66 to different sets of Shelf Support Apertures 80 at the same level.

A Cabinet Door Gasket 130 made of heat-resistant silicone or other suitable material, located inside the Cabinet Door 120, is intended to create an airtight seal between the Cabinet Door 120 an the Interior Cabinet Face 142 around the perimeter of a Cabinet Aperture 140 when the Cabinet Door 120 is closed to cover sealably said Cabinet Aperture 140 and a Cabinet Door Closure 124 or other cabinet securing means is engaged. Security integrity means, such as a Closure Integrity Lock 26 (not illustrated in FIG. 20), additionally may be employed.

Figure 20:
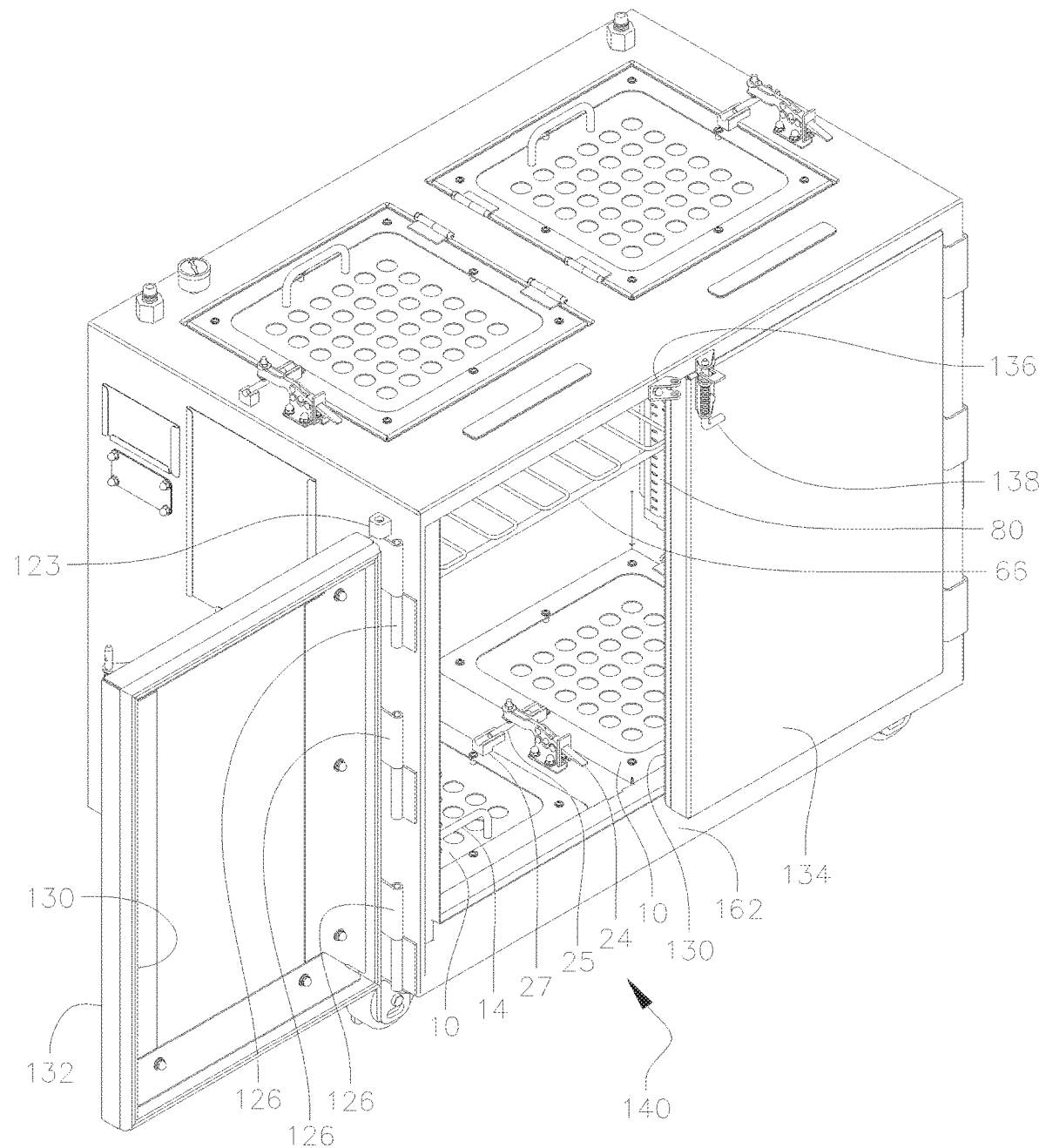
FIG. 20 is a front left top isometric view of a particular embodiment of a Cabinet 2 with both a Left Cabinet Door 132 and a Right Cabinet Door 134.

The embodiment in FIG. 20 utilizes a two-door design, with a Left Cabinet Door 132 and a Right Cabinet Door 134 meeting at the center of the Cabinet 2 over a Cabinet Aperture 140, and one or more Cabinet Door Hinges 126 hingeably attaching each such door to the Cabinet 2. Both the Left Cabinet Door 132 and the Right Cabinet Door 134 may have a cabinet securing means such as the illustrated Cabinet Door Closure 124, comprised of a Cabinet Door Closure Female Element 136 and a Cabinet Door Closure Male Element 138. A Cabinet Door Gasket 130 on the interior of both the Left Cabinet Door 132 and the Right Cabinet Door 134 may be employed to create an airtight seal between each of these doors 132, 134 and the Cabinet 2, as well as between the doors 132, 134 themselves. Additionally, a gasket of suitable material such as heat-resistant silicone (not illustrated) may be interposed between the doors 132, 134 to effectuate better sealing.

Figure 9:
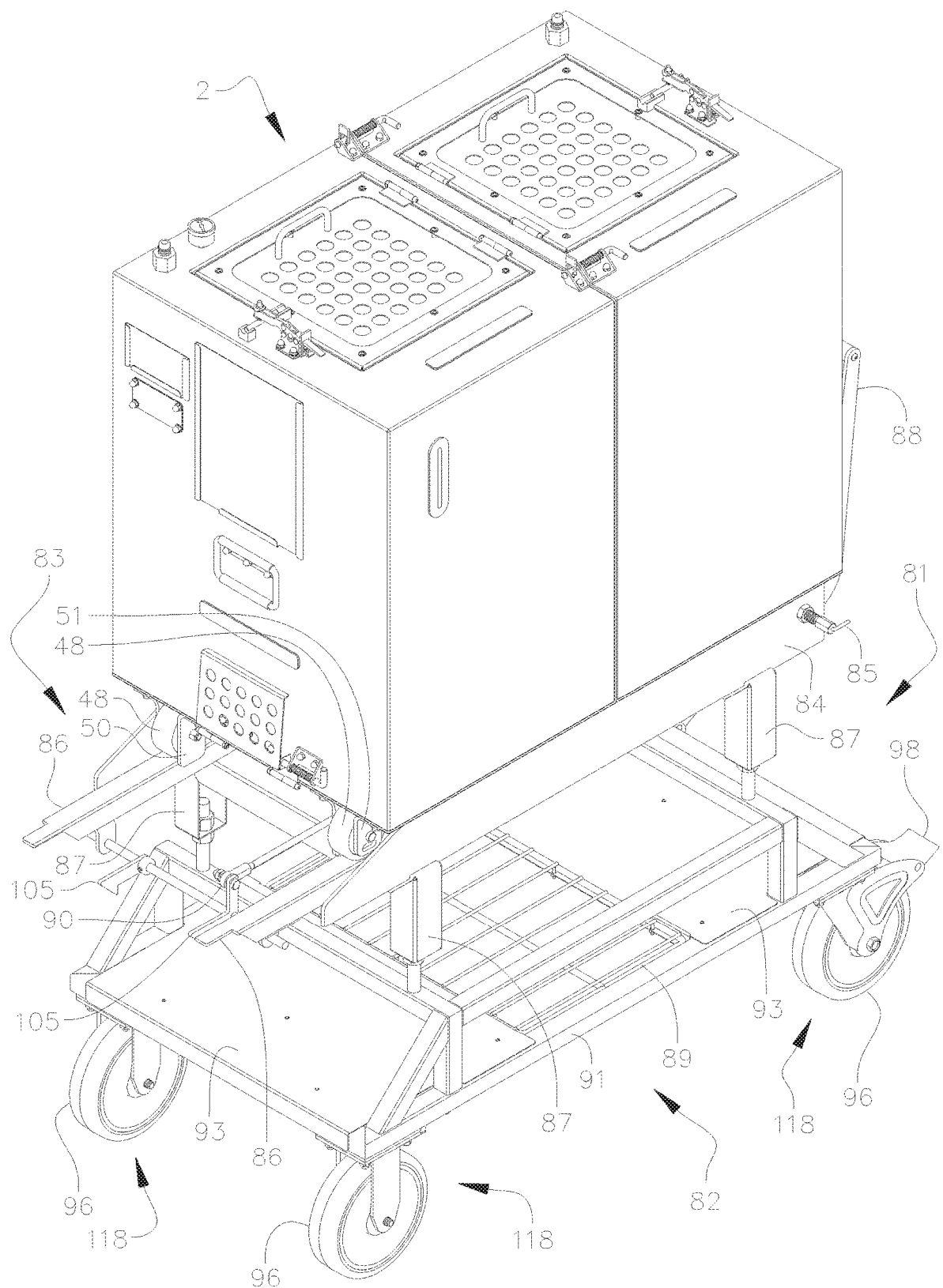
FIG. 9 is a front left top isometric view of a clamshell-style embodiment of a Cabinet 2 secured on one particular embodiment of a Transfer Cart 81.

In FIG. 9, one possible embodiment of a Transfer Cart 81 is depicted with a clamshell-style embodiment of a Cabinet 2 secured thereon. The Transfer Cart 81 shown comprises a Transfer Cart Frame 91, consisting of a Transfer Cart Lower Assembly 82 and a Transfer Cart Upper Assembly 83. A Transfer Cart Lower Assembly 82 may incorporate a wire-style Transfer Cart Shelf 89 in the center, on either end of which may be a Transfer Cart Solid Shelf 93. Attached to the Transfer Cart Frame 91 is a plurality of removable Transfer Cart Wheel Assemblies 118. Each Transfer Cart Wheel Assembly 118 may include a Transfer Cart Wheel Lock 98 to arrest temporarily the motion of a Transfer Cart Wheel 96.

A Transfer Cart Upper Assembly 83 comprises a Transfer Cart Dock 84 into which a Cabinet 2 may be inserted. The Transfer Cart Dock 84 may be supported by a plurality of Transfer Cart Levelers 87. Each such Transfer Cart Leveler 87 has adjustment means, which typically may comprise two or more nuts about a vertical threaded shaft, allowing the level of the Transfer Cart Dock 84 and any Cabinet 2 therein to be leveled. The term 'adjustment means' as utilized herein is intended to include any structure that can be employed to carry out the function of making a Cabinet 2 level within a Transfer Cart Dock 84 or a Lift Dock 110, whether or not such a structure is recited with particularity herein.

A Cabinet 2 is situated in the Transfer Cart Dock 84 with its Cabinet Wheels 48 resting on Transfer Cart Connecting Rails 86 within the Transfer Cart Dock 84, which Transfer Cart Connecting Rails 86 may be vertically and horizontally adjustable and at one end are tapered, allowing them to mate or pair with companion rails on a standard industrial autoclave and with Lift Rails 109 on a Lift Device 100. The Long Safety Retention Tabs 50 are intended to ensure that the Cabinet Wheels 48 remain on and are guided by the Transfer Cart Connecting Rails 86. A Transfer Cart Dock 84 typically will include one or more Cabinet Pins 85, each of which may be inserted into a Short Safety Retention Tab with Slot 51 to secure a Cabinet 2 to and integrate a Cabinet 2 with the Transfer Cart 81. A Transfer Cart Handle 88 serves to facilitate moving the Transfer Cart 81 and any Cabinet 2 therein through pushing and pulling, or a combination thereof. A Transfer Cart Integrated Autoclave Locking Mechanism 90 with one or more Autoclave Locking Hooks 105 allows the Transfer Cart 81 to be secured to and unsecured from an industrial autoclave.

Figure 10:
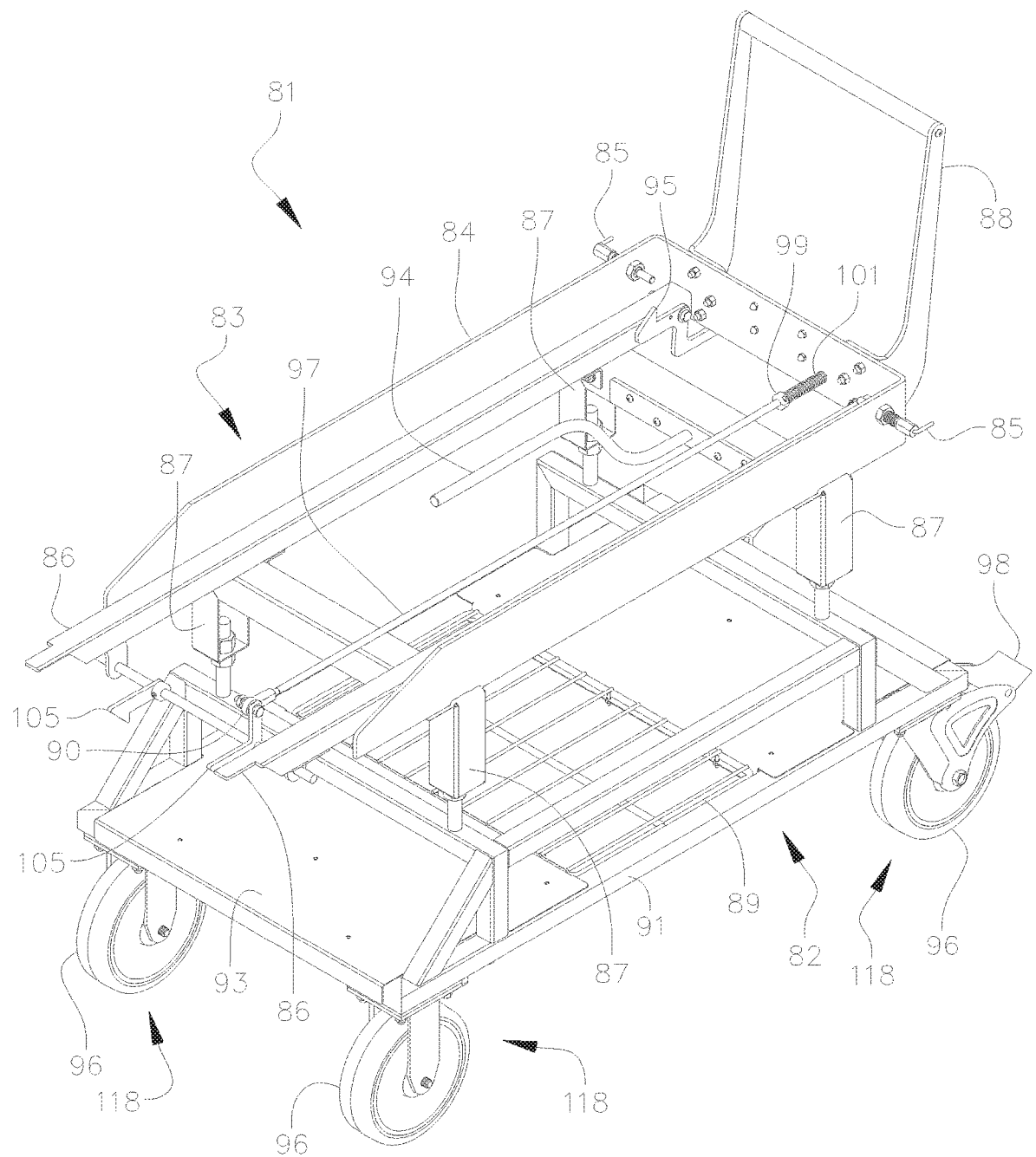
FIG. 10 is a front left top isometric view illustrating a particular embodiment of a Transfer Cart 81.

In FIG. 10, the Transfer Cart Integrated Autoclave Locking Mechanism is more fully revealed, showing an Autoclave Disengaging Rod 97 that, when pulled, causes each Autoclave Locking Hook 105 to disengage from a standard industrial autoclave by raising any said Autoclave Locking Hook 105 and thereby unsecure the Transfer Cart 81 for removal from the autoclave. An Autoclave Disengaging Rod Spring 101 is disposed about a portion of the Autoclave Disengaging Rod 97 between the inside of the Transfer Cart Dock 84 and an Autoclave Disengaging Rod Collar 99 affixed to the Autoclave Disengaging Rod 97, causing the Autoclave Disengaging Rod 97 to remain in a fully forward position when not being pulled to raise each Autoclave Locking Hook 105.

A Cabinet Safety Lock 95, in combination with any Cabinet Safety Pin 85, may provide a redundant means of integrating and securing the Cabinet 2 to the Transfer Cart 81 by engaging with a Long Safety Retention Tab 50. A Transfer Cart Stabilization Rod 94, inserted into a Cabinet Stabilization Rod Bracket 53, may provide yet another means of ensuring that a Cabinet 2 is well secured to the Transfer Cart 81.

Figure 11:
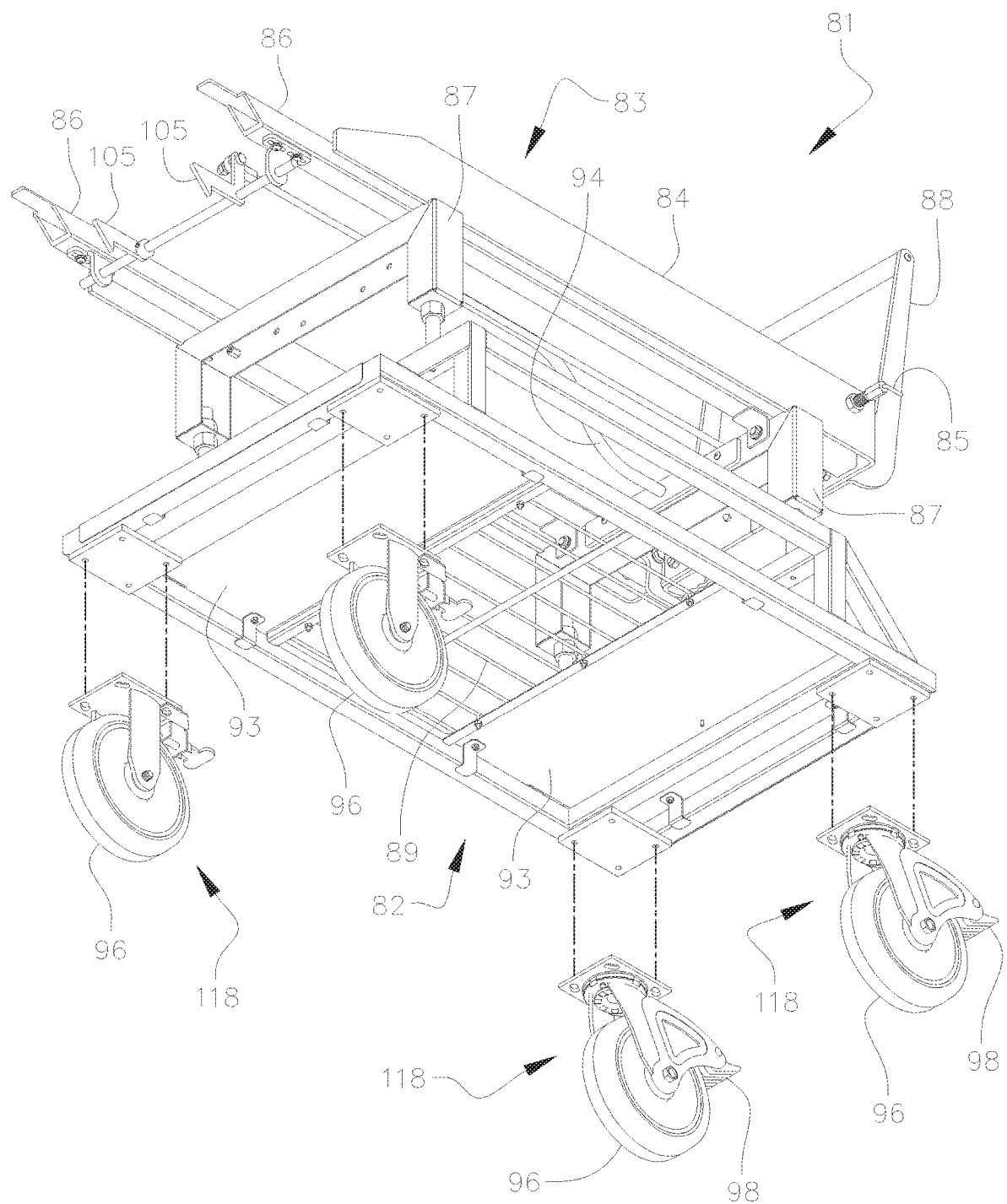
FIG. 11 is a front left bottom isometric view of a particular embodiment of a Transfer Cart 81 reflecting the removable character of each Transfer Cart Wheel Assembly 118.

FIG. 11 reflects the removable character of any Transfer Cart Wheel Assembly 118. Each Transfer Cart Wheel Assembly 118, including any Transfer Cart Wheel 96 and Transfer Cart Wheel Lock 98 of which it may be comprised, may be removed.

Figure 12:
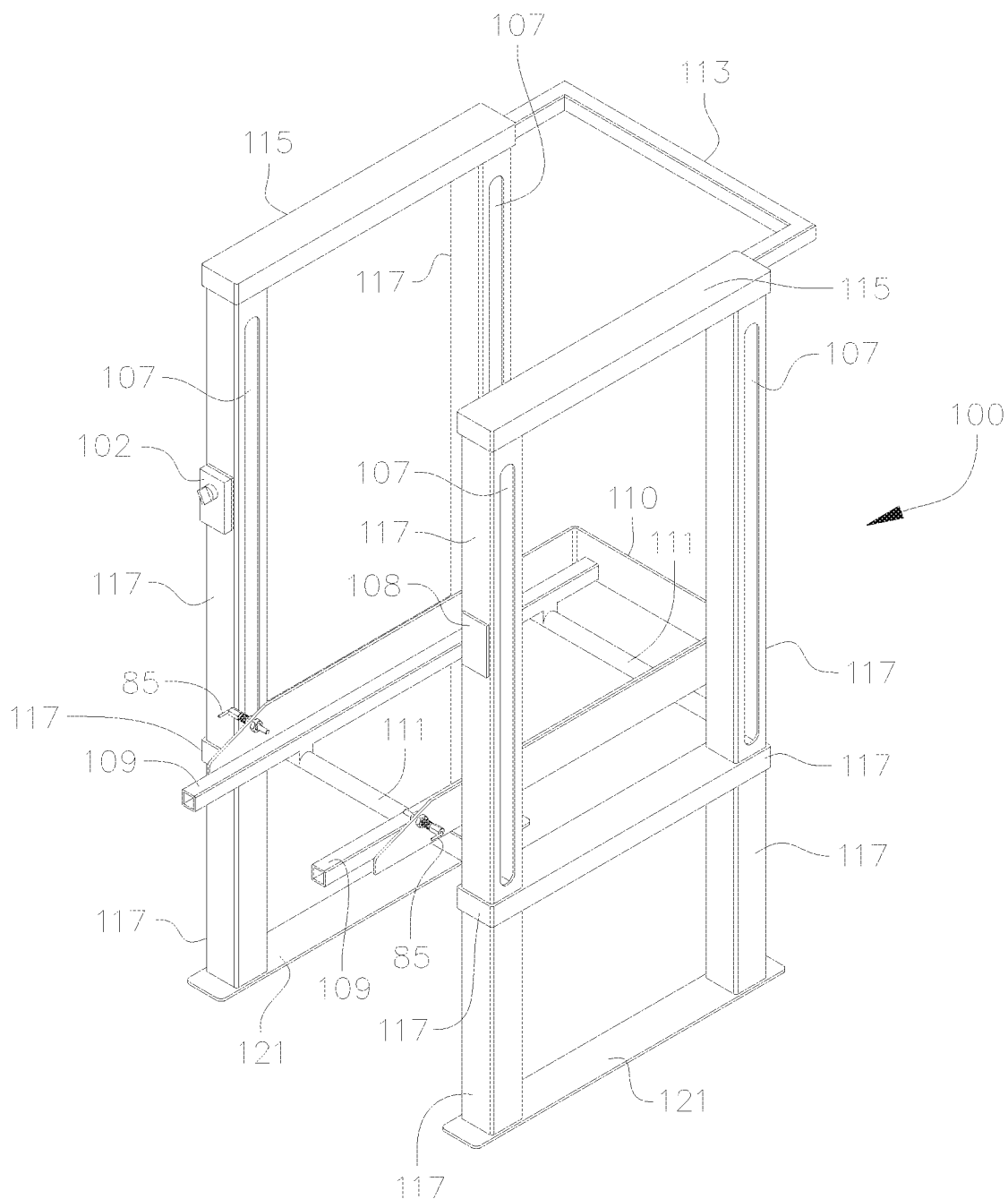
FIG. 12 is a front right top isometric view of a particular embodiment of a Lift Device 100.

A Lift Device 100 is pictured in FIG. 12, comprising at least two Lift Device Frames 117 as well as at least one Safety Retention Bar 113 joining Lift Device Frames 117 and at least two Modular Connection Caps 115 to secure the at least one Safety Retention Bar 113 to the Lift Device Frames 117. A Modular Connection Cap 115 additionally can be used to extend the capacity of a Lift Device 110 by serving to secure two Safety Retention Bars 113 to a common Lift Device Frame 117. One or more Lift Frame Base Plates 121 attached to the bottom of a Lift Device Frame provide stability to a Lift Device Frame 117 as well as to the overall Lift Device 100. A Lift Device Frame, Safety Retention Bar, Modular Connection Cap, and Lift Frame Base Plate may be made from stainless steel, other metal or synthetic materials, or indeed, any other suitable materials or combinations of such materials whatsoever.

At least one Lift Dock 110 capable of accepting a Cabinet 2 (illustrated in subsequent figures) is supported by one or more Lift Support Bars 111, the ends of which extend into Lift Channels 107 in the Lift Device Frame 117, allowing the Lift Dock 110 and any Cabinet 2 therein to move vertically with respect to a Lift Device Frame 117. The removable Cabinet Wheels 48 of any Cabinet 2 situated in the Lift Dock 110 rest on Lift Rails 109. Each Lift Rail 109 may be adjustable both vertically and horizontally, and has an open end to accept the tapered end of a Transfer Cart Connecting Rail 86. At least one Cabinet Safety Pin 85 may be employed to secure a Cabinet 2 to a Lift Dock 110.

A Lift Device 100 is intended to accommodate lift control means, which may be mechanical or electronic in nature and operated from a Lift Control Panel 102 to control lift power means, such as an electric motor, hydraulic, or pneumatic system (not pictured) in combination with lift means, such as a screw mechanism, cable system or scissor jack mechanism (not pictured) to accomplish the raising or lowering of the one or more Lift Support Bars 111 supporting a Lift Dock 110, and hence, the raising and lowering of the Lift Dock 110 and any Cabinet 2 therein. The term 'lift control means' as utilized herein is intended to include any structure that can be employed to carry out the function of controlling a lift power means, the term 'lift power means' as used herein means to include any structure that can be employed to power a lift means, and the term 'lift means' is intended to include any structure that can be employed to carry out the function of raising and lowering a Lift Dock 110 and any Cabinet 2 therein via one or more Lift Support Bars 111, whether or not any such structure are recited with particularity herein.

The Lift Device Frame will typically have at least two locations for the placement and installation of a Lift Device Control Panel 102 in the Lift Device Frame 117, one on either side of the Lift Dock 110, to enhance the modular character of the Lift Frame Device 100. A Plate 108 may be placed at any unused location for the placement and installation of a Lift Device Control Panel 102.

Figure 13:
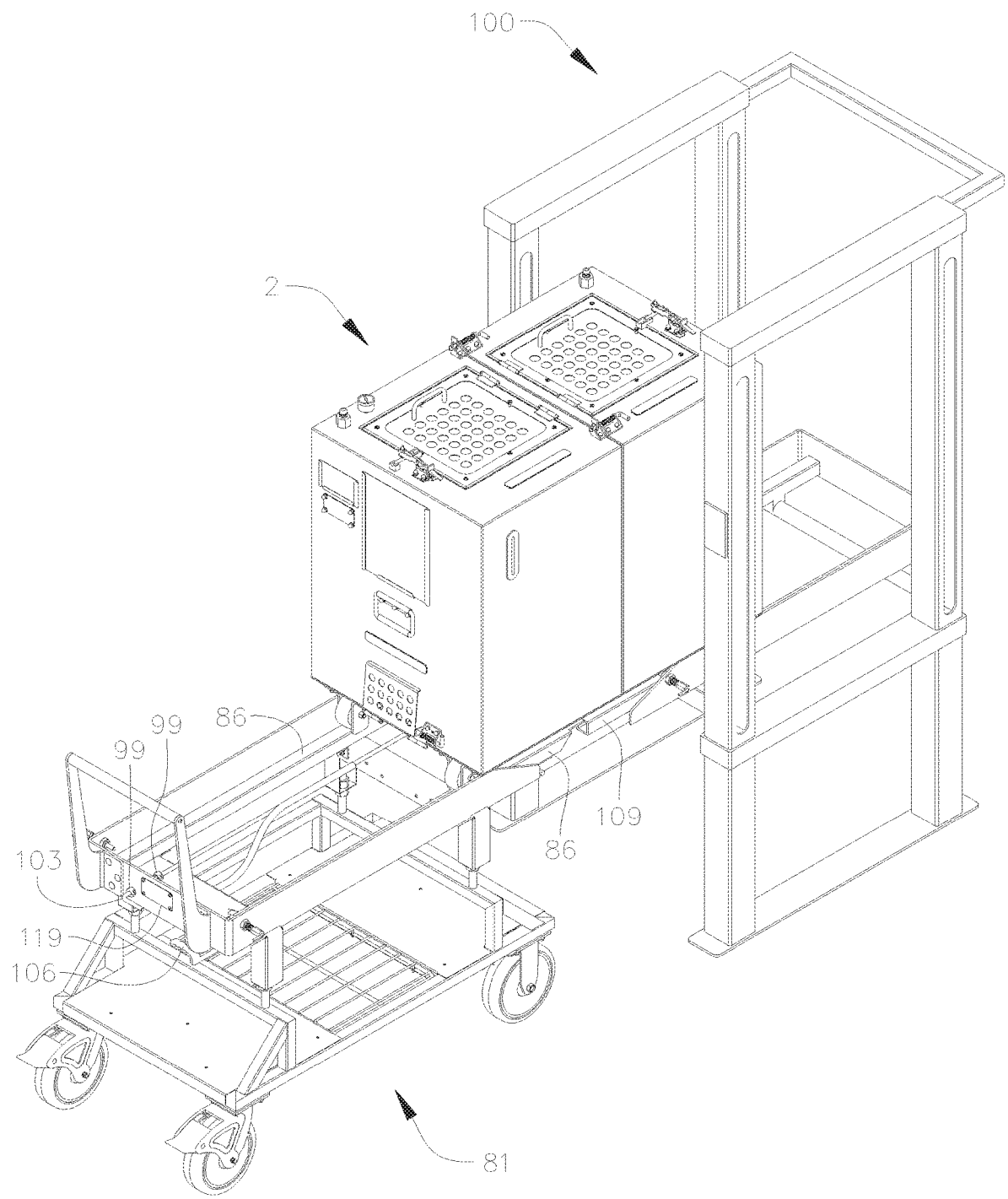
FIG. 13 is a front right top isometric view of a particular embodiment of a Lift Device 100 illustrating how a Cabinet 2 may be transferred between a Transfer Cart 84 and the Lift Device 100.

FIG. 13 illustrates the manner in which a Cabinet 2 may be conveyed between a Transfer Cart 81 and a Lift Device 100, reflecting how the tapered end of a Transfer Cart Connecting Rail 86 may be lined up for insertion into the hollow end of a Lift Rail 112 to allow a Cabinet 2 to roll between a Transfer Cart Dock 84 and a Lift Dock 110. Further illustrated is an Autoclave Disengaging Rod Handle 103 that may be used to pull the Autoclave Disengaging Rod 97 to disengage any Autoclave Locking Hook 105 from an industrial autoclave and thus unsecure from the autoclave the Transfer Cart 81, as well as a Cabinet Safety Lock Handle 106 to engage and disengage the Cabinet Safety Lock 95 to and from a Long Safety Retention Tab 50. A Transfer Cart Serial Number Plate 119 may be affixed to a Transfer Cart Dock 84 or elsewhere on a Transfer Cart 81 for purposes of identification.

Figure 14:
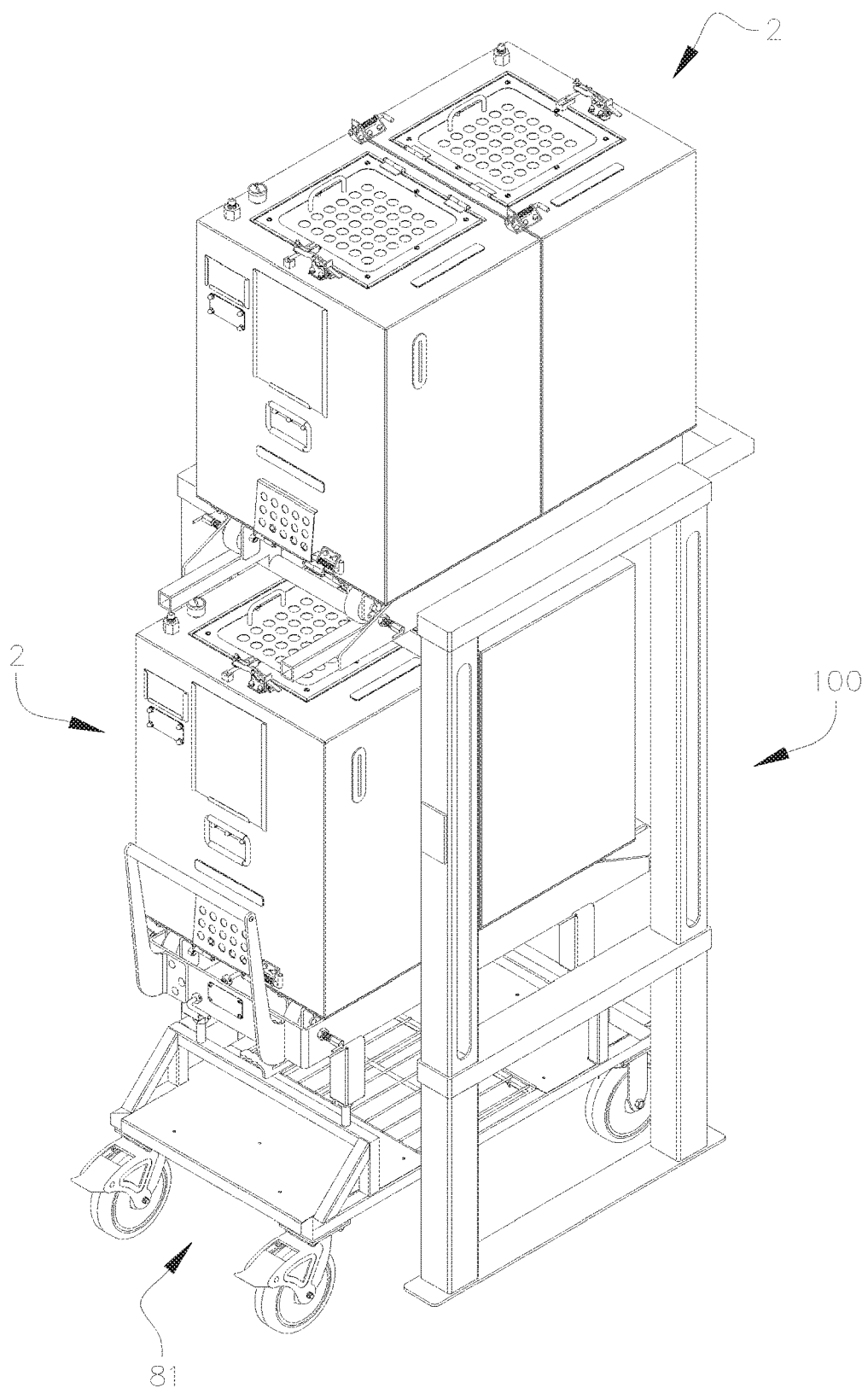
FIG. 14 is a front right top isometric view of a particular embodiment of a Lift Device showing how Cabinets 2 may be stored vertically using the Lift Device 100.

FIG. 14 demonstrates the manner in which Cabinets 2 may be stacked vertically and stored within the Lift Device 100. In the embodiment illustrated a Transfer Cart 81 with a Cabinet 2 in its Transfer Cart Dock 84 is also stored within the Lift Device 100, obviating the need for more than one Lift Dock 110.

Figure 15:
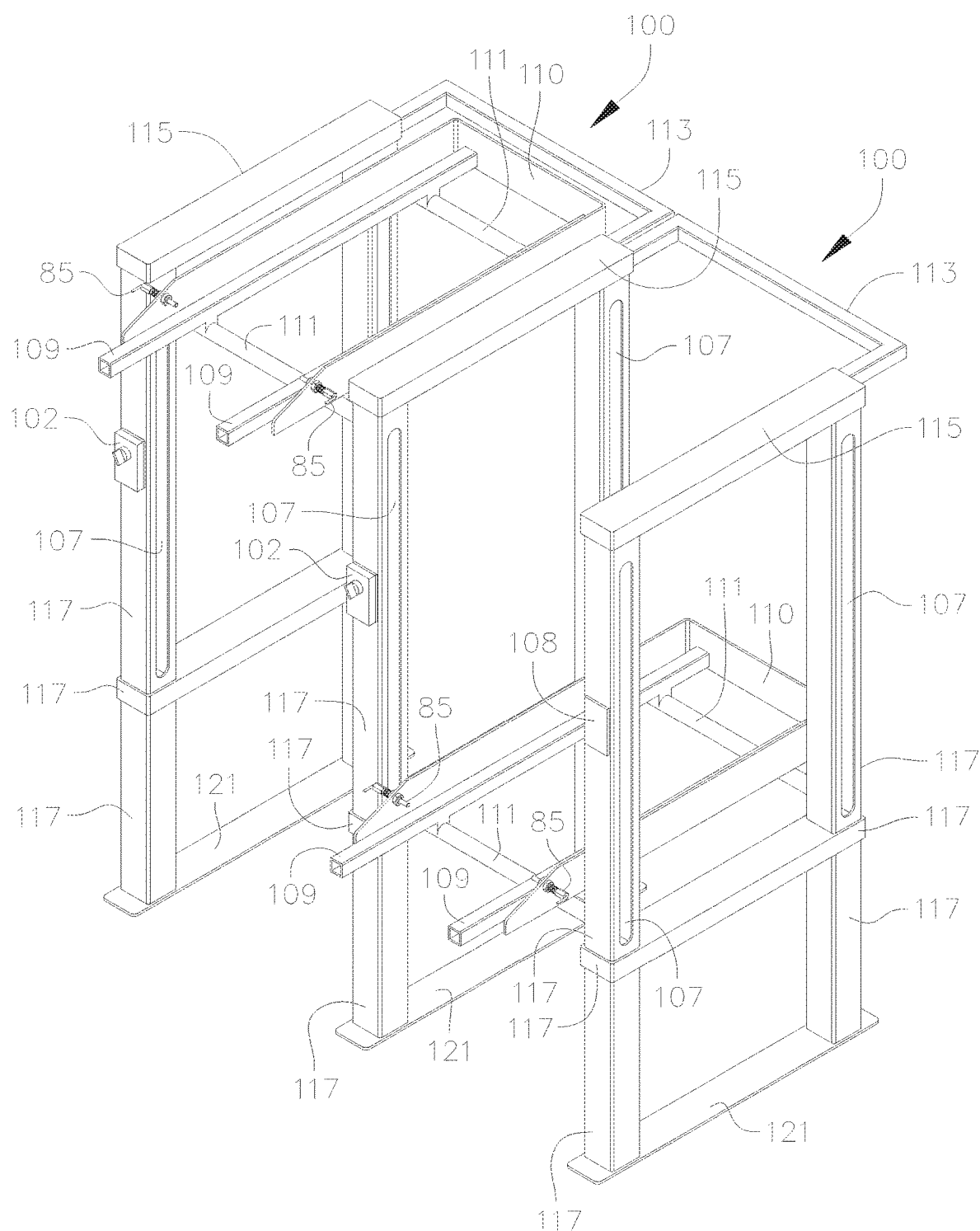
FIG. 15 is a front right top isometric view of three Lift Device Frames 117 joined together to reflect the modular design and functionality of a Lift Device 100.

FIG. 15 shows the modular character of one embodiment of a Lift Device 100. Three Lift Device Frames 117 are connected via two Safety Retention Bars 113 sharing a Modular Connection Cap 115. Each Lift Dock 110 is raised and lowered using its own Lift Control Panel 102. The illustrated configuration allows for storage of up to four Cabinets 2 and two Transport Carts 81.

Figure 16:
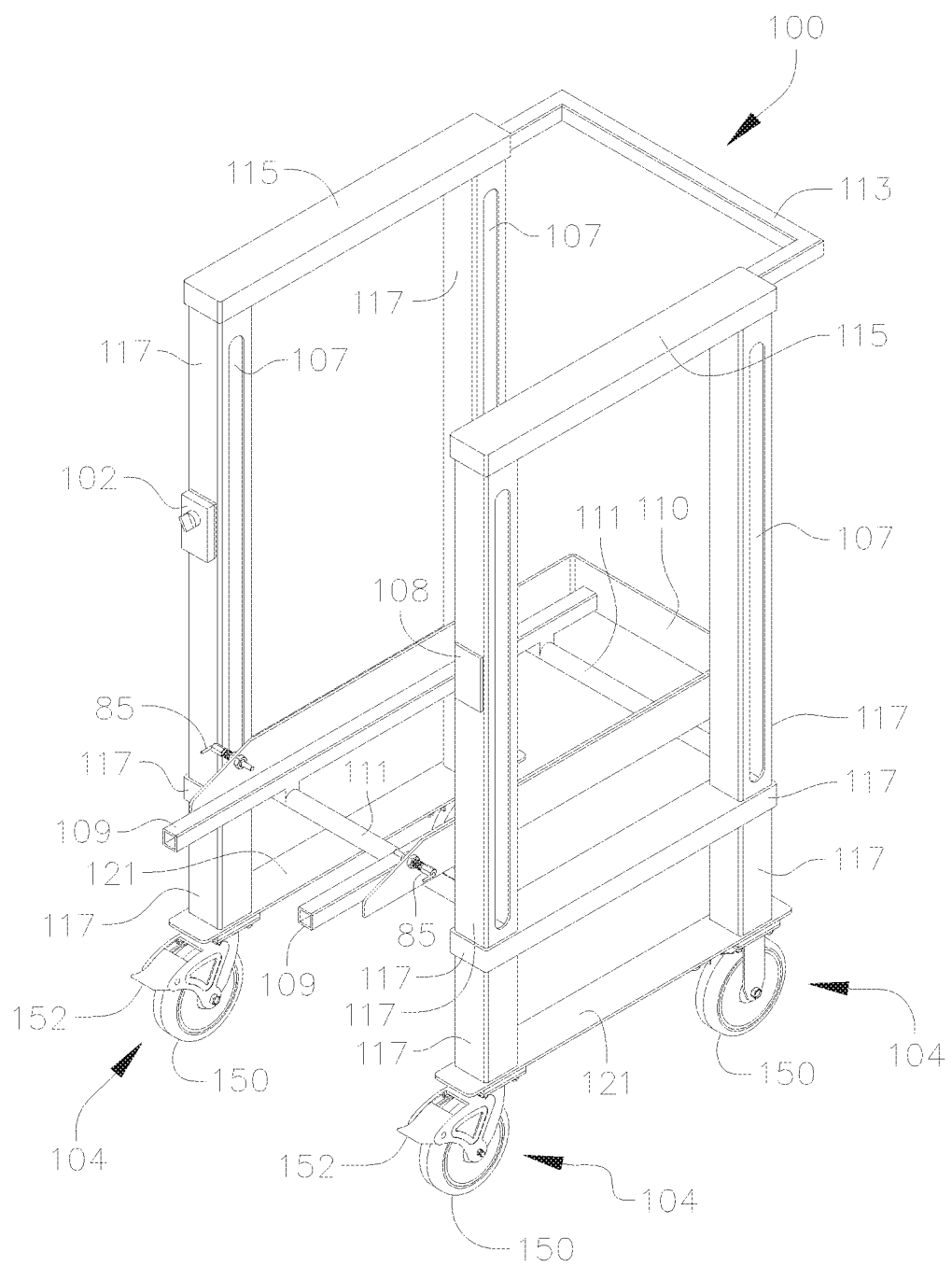
FIG. 16 is a front right top isometric view of a particular embodiment of a Lift Device 100 with Lift Device Wheel Assemblies 104 attached to the Lift Device Frame 117 via the Lift Frame Base Plate 121.

In FIG. 16, removable Lift Device Wheel Assemblies 104 have been connected to the bottom of the Lift Device Frame Base Plate 121 to allow the Lift Device 100 to be easily moved. Alternatively, a Lift Device Wheel Assembly 104 may be connected to a Lift Frame 117 through a Lift Frame Base Plate 121, or directly to a Lift Device Frame 117 by first removing any Lift Device Frame Baseplate 121 from the bottom of the Lift Device Frame 117. A Lift Device Wheel Assembly 104 comprises a Lift Wheel 150, and may further comprise a Lift Wheel Lock 152 to arrest temporarily the motion of a Lift Wheel 150.

The Cabinet 2 as described allows for an improved method of sterilization of surgical trays. First, gaskets may be examined and replaced as necessary or desired. In the case of a clamshell-style embodiment of a Cabinet 2, any Clamshell Gaskets 64 may be inspected and replaced if necessary or desired. With respect to door-style embodiments of a Cabinet 2, Cabinet Door Gaskets 130 may be replaced as necessary or desired, as well as any gasket between a Left Cabinet Door 132 and a Right Cabinet Door 134. Filter Well Vented Door Gaskets may also be inspected and replaced as necessary or desired.

Next, a Cabinet 2 is prepared for sterilization by installing any necessary or desired Filters 56 (Filters 56 may, but need not, be used if sterilization is to be conducted with Ethylene Oxide (ETO) gas). The installation of Filters 56 is accomplished, with respect to each Filter Well Vent Door 10, by disengaging each Filter Well Vent Door Cam-Lock 24 or other locking means so as to unlock the Filter Well Vent Door 10, opening each Filter Well Vent Door 10, inserting a Filter 56 within each Filter Well 58, closing each Filter Well Vent Door 10, engaging each locking means, such as a Filter Well Vent Door Cam-Lock 24, and installing security integrity means, such as a Closure Integrity Lock 28.

At this point, a Cabinet 2 may be closed and secured until it is time to proceed with sterilization. In the case of a clamshell version of a Cabinet 2, this may accomplished by pivoting a Left Cabinet Portion and a Right Cabinet Portion towards one another, then engaging the Clamshell Closure 18 or other cabinet securing means to hold fast the Cabinet 2. In the case of a door embodiment, the Cabinet Door(s) 120 is/are closed and the Cabinet Door Closure 124 or other cabinet securing means engaged. When it is time for sterilization, the Cabinet 2 may again be opened as described above.

When it is time for sterilization, surgical trays and their respective contents are then inserted into the Cabinet 2 as prepared above and onto Shelves 66 that have already been installed within the Cabinet 2 at the desired level(s). Chemical Indicator Stickers 28 may at this point be inserted within the interior of the Cabinet B, which is then closed as described above, and the Clamshell Closure 18, Cabinet Door Closure 124, or other cabinet securing means engaged. At this point, Closure Integrity Locks 26 or other security integrity means may be engaged with respect to the Clamshell Closure 18, Cabinet Door Closure 124, or other cabinet securing means, as applicable.

One or more supply lines for a sterilization agent is/are then attached to one or more Inlet Couplers 34, and one or more vacuum lines are attached to one or more Outlet Couplers 62. The sterilization agent, which may be steam, ETO, or another appropriate substance, is then introduced into the Cabinet 2 through the one or more Inlet Coupler(s) 34 in an effective amount for a period of time sufficient to achieve sterilization of the interior of the Cabinet 2 and its contents, following which said sterilization agent may be extracted from the Cabinet 2 via one or more Outlet Couplers 62. The supply and vacuum lines are then removed from the one or more Inlet Couplers 34 and the one or more Outlet Couplers 62, respectively. The contents of the Cabinet 2 are now sterilized and ready for use. The Cabinet 2 may be taken to storage until it is time to use the sterilized surgical tray or trays and their contents.

We claim:

1. A method of sterilizing at least one surgical tray containing at least one surgical instrument using a cabinet, where the cabinet is sized to receive the at least one surgical tray within an interior sterilization chamber, where the cabinet can be opened for insertion and removal of at least one surgical tray into the interior sterilization chamber and the cabinet includes a sealed configuration with the at least one surgical tray located therein, the method comprising:
   opening the cabinet;
   loading the at least one surgical tray containing the at least one surgical instrument into the interior sterilization chamber;
   securing the cabinet into the sealed configuration and engaging a security integrity mechanism when securing the cabinet into the sealed configuration wherein the security integrity mechanism includes an indicator to ascertain a sterilization status of the cabinet;
   positioning of the cabinet at a sterilization location adjacent to an autoclave using a transfer cart;
   securing the transfer cart to prevent movement of the transfer cart;
   transferring the cabinet from the transfer cart into the autoclave using mechanical guides;
   sterilizing the at least one surgical instrument within the interior sterilization chamber;
   positioning the cabinet onto the transfer cart while the cabinet is in the sealed configuration; and
   relocating the cabinet from the sterilization location using the transfer cart, while in the sealed configuration such that the at least one surgical instrument remains sterile.

2. The method of claim 1, where loading the at least one surgical tray comprises loading the at least one surgical tray in an unwrapped condition.

3. The method of claim 1, wherein the cabinet comprises a plurality of surgical instruments in a plurality of trays.

4. The method of claim 1, further comprising locking the transfer cart relative to the autoclave from a side of the transfer cart that is opposite to the autoclave.

5. The method of claim 1, further comprising locking the cabinet relative to the transfer cart.

6. The method of claim 1, further comprising inspecting a gasket between a door of the cabinet and the cabinet.

7. The method of claim 6, further comprising replacing the gasket.

8. The method of claim 1, further comprising installing at least one filter onto the cabinet.

9. The method of claim 1, wherein the transfer cart comprises:
   one or more locking hooks to engage the autoclave; and
   one or more wheel locks.

10. The method of claim 1, where the cabinet is constrained to move in alignment with the mechanical guides to guide the cabinet into the autoclave.

11. The method of claim 1 wherein securing the transfer cart to prevent movement of the transfer cart comprises positioning the cabinet adjacent to the autoclave such that one or more locking hooks engage the autoclave.

12. The method of claim 11 wherein the one or more locking hooks comprise two spaced-apart locking hooks.

13. The method of claim 5 wherein locking of the transfer cart to the cabinet comprises:
   engaging a cabinet safety lock mechanism; and
   engaging a cabinet safety pin.

14. The method of claim 4 further comprising locking the cabinet relative to the transfer cart by engaging a cabinet safety lock mechanism.

15. The method of claim 14 further comprising:
    releasing the cabinet relative to the transfer cart prior to transferring the cabinet into the autoclave, by disengaging the cabinet safety lock mechanism.

16. The method of claim 15 further comprising releasing the transfer cart from the autoclave prior to relocating the cabinet from the sterilization location using the transfer cart.

17. The method of claim 16 wherein the transfer cart is released from the autoclave using an autoclave disengaging handle that is located on a side of the transfer cart opposite the autoclave.

18. The method of claim 17 wherein the cabinet is released relative to the transfer cart using a cabinet safety lock handle that is located on a side of the transfer cart opposite the autoclave.

* * * * *